(12) United States Patent
Sarkar et al.

(10) Patent No.: US 11,752,289 B2
(45) Date of Patent: Sep. 12, 2023

(54) SYSTEM AND METHOD FOR AUTOMATIC EMERGENCY AIRWAY DETECTION

(71) Applicant: University Of Maryland, Baltimore, Baltimore, MD (US)

(72) Inventors: Rajabrata Sarkar, Ellicott City, MD (US); Jeffrey S. Wolf, Owings Mills, MD (US); Aldo T. Iacono, Cockeysville, MD (US); Stephen Restaino, Columbia, MD (US); Riddhi Gopal, Baltimore, MD (US)

(73) Assignee: University Of Maryland, Baltimore, Baltimore, MD (US)

( * ) Notice: Subject to any disclaimer, the term of this patent is extended or adjusted under 35 U.S.C. 154(b) by 845 days.

(21) Appl. No.: 16/707,949

(22) Filed: Dec. 9, 2019

(65) Prior Publication Data

US 2020/0179631 A1   Jun. 11, 2020

Related U.S. Application Data

(60) Provisional application No. 62/776,614, filed on Dec. 7, 2018, provisional application No. 62/915,244, filed on Oct. 15, 2019.

(51) Int. Cl.
| | |
|---|---|
| *A61M 16/04* | (2006.01) |
| *A61B 17/34* | (2006.01) |
| *A61M 16/00* | (2006.01) |

(52) U.S. Cl.
CPC ..... *A61M 16/0472* (2013.01); *A61B 17/3415* (2013.01); *A61M 16/0003* (2014.02);
(Continued)

(58) Field of Classification Search
CPC .... A61M 16/00; A61M 16/003; A61M 16/04; A61M 16/0402; A61M 16/0463;
(Continued)

(56) References Cited

U.S. PATENT DOCUMENTS

| | | | | |
|---|---|---|---|---|
| 3,991,765 A | * | 11/1976 | Cohen ............... | A61M 16/0472 128/207.29 |
| 8,356,598 B2 | * | 1/2013 | Rumsey ............ | A61M 16/0472 128/207.29 |

(Continued)

OTHER PUBLICATIONS

Kotwal et al., Eliminating Preventable Death on the Battlefield, Arch Surg, 2011, pp. 1350-1358, vol. 146.
(Continued)

*Primary Examiner* — Colin W Stuart
(74) *Attorney, Agent, or Firm* — Wolter Van Dyke Davis, PLLC; Eugene J. Molinelli; Cian G. O'Brien

(57) ABSTRACT

A method and apparatus is provided for automatic emergency airway detection. The apparatus includes a frame with a carriage guide configured to be secured around a neck of a subject. A carriage including a sensor is configured to move along the carriage guide. The sensor is configured to measure a value of a parameter indicating a topography of the neck of the subject. A processor includes a memory with instructions to receive first data from the sensor of the value of the parameter as the carriage is moved along the carriage guide and to determine, with the first data, second data indicating a position along the carriage guide corresponding to the cricothyroid region of the neck. The processor subsequently transmits a first signal indicating the second data. A method of using the apparatus is also provided.

25 Claims, 16 Drawing Sheets

(52) U.S. Cl.
CPC ... *A61M 16/024* (2017.08); *A61M 2205/3327* (2013.01); *A61M 2205/50* (2013.01); *A61M 2210/065* (2013.01); *A61M 2210/1032* (2013.01)

(58) Field of Classification Search
CPC ............ A61M 16/048; A61M 16/0472; A61M 16/024; A61M 16/022; A61M 16/021; A61M 2205/3327; A61M 2205/33; A61M 2205/50; A61B 17/3415; A61B 34/20; A61B 2560/0462; A61B 2562/0257; A61B 2562/0261; A61B 2562/0252; A61B 2562/04; A61B 5/065; A61B 5/68; A61B 5/684; A61B 5/6885; A61B 8/4245; A61B 8/4254; A61B 8/4263
See application file for complete search history.

(56) References Cited

U.S. PATENT DOCUMENTS

| | | | | |
|---|---|---|---|---|
| 2005/0039755 | A1* | 2/2005 | Gooden | A61M 16/0472 128/207.14 |
| 2008/0251083 | A1* | 10/2008 | Fetcenko | A61M 16/0472 128/207.29 |
| 2009/0229602 | A1* | 9/2009 | Single, Jr. | A61M 16/0472 128/207.29 |
| 2011/0263935 | A1* | 10/2011 | Qiu | G06F 18/2415 382/128 |
| 2012/0149980 | A1* | 6/2012 | Pacey | A61B 1/267 600/109 |
| 2014/0121637 | A1* | 5/2014 | Boyden | A61M 5/427 604/116 |
| 2015/0182716 | A1* | 7/2015 | Wolf | A61M 16/0486 128/207.14 |
| 2016/0220772 | A1* | 8/2016 | Krimsky | A61M 16/0488 |
| 2016/0310006 | A1* | 10/2016 | Aguero Villarreal | A61B 5/4538 |

OTHER PUBLICATIONS

Pugh et al., A review of pre-admission advanced airway management in combat casualties, Helmand Province 2013, J. R. Army Med, 2015, pp. 121-126j, vol. 161.
Pitts et al., Brain Death, Apneic Diffusion Oxygenation, and Organ Transplantation., J. Trauma Acute Care Surg., 1978, pp. 180-183, vol. 18.
Wolf et al., Intrabronchial Catheter Resuscitation for Respiratory and Cardiorespiratory Arrest, Shock, 2018, pp. 96-102, vol. 50.
Langvad et al., Emergency cricothyrotomy—a systematic review, Scand J Trauma Resusc Emerg Med, 2013, pp. 1-14, vol. 21.

* cited by examiner

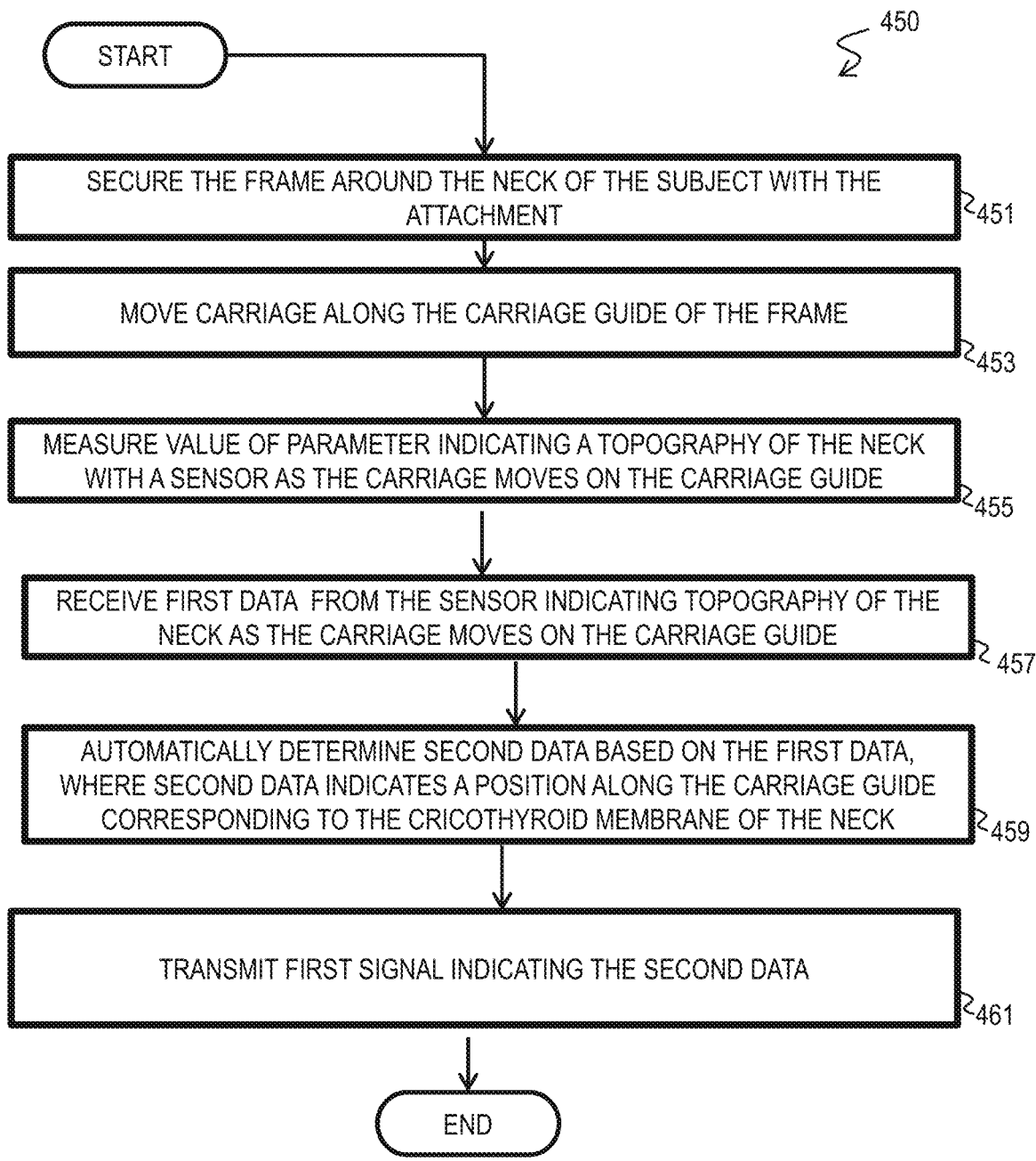

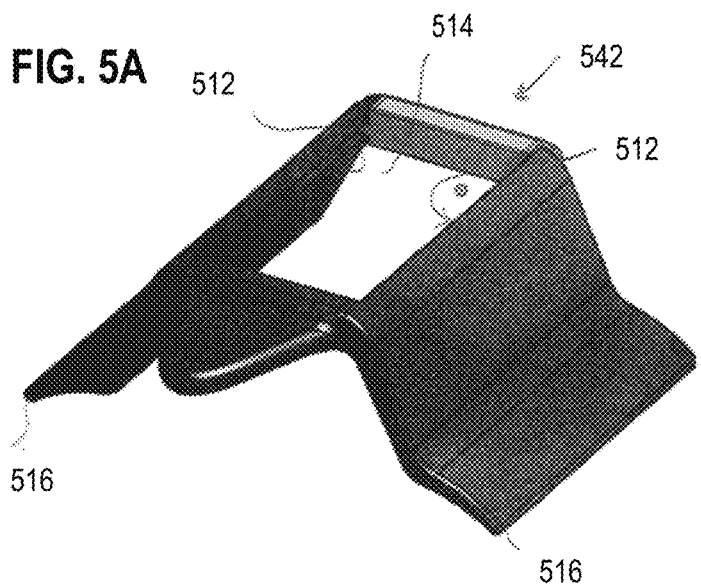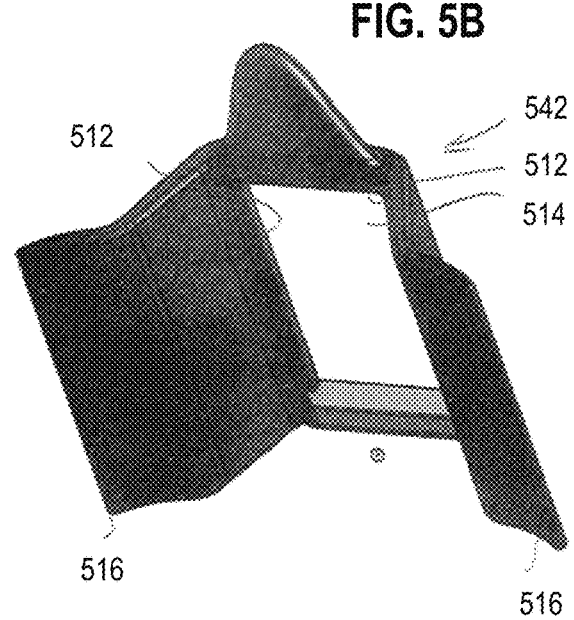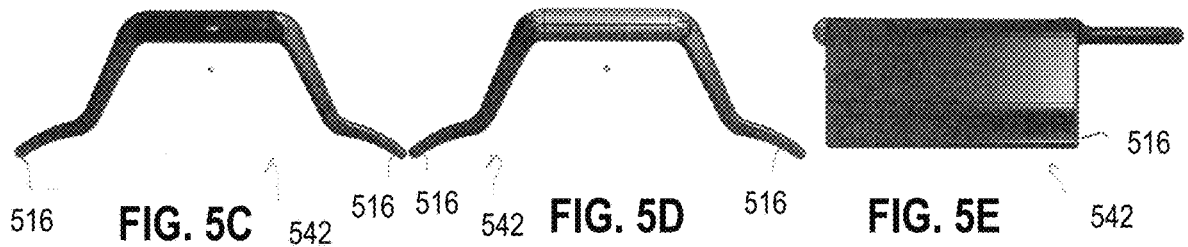

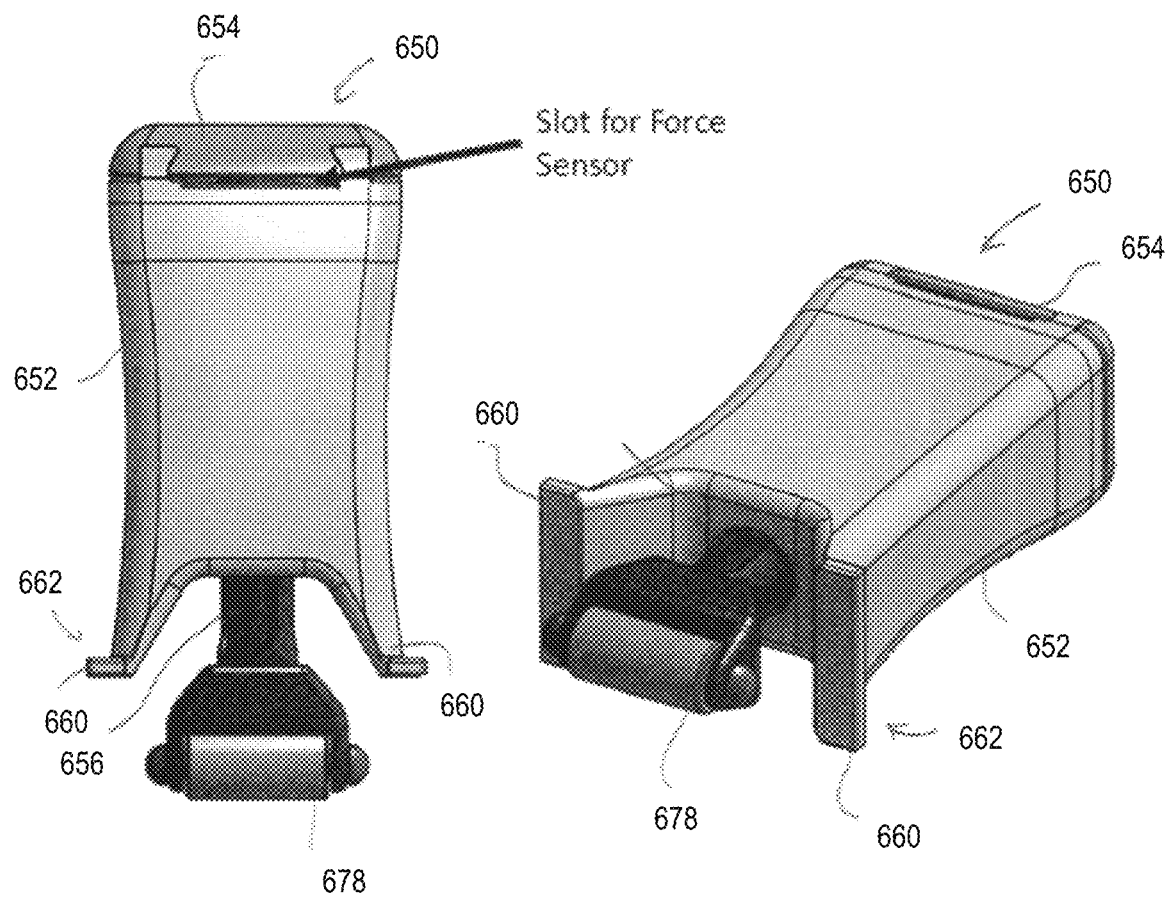
FIG. 6A
FIG. 6B
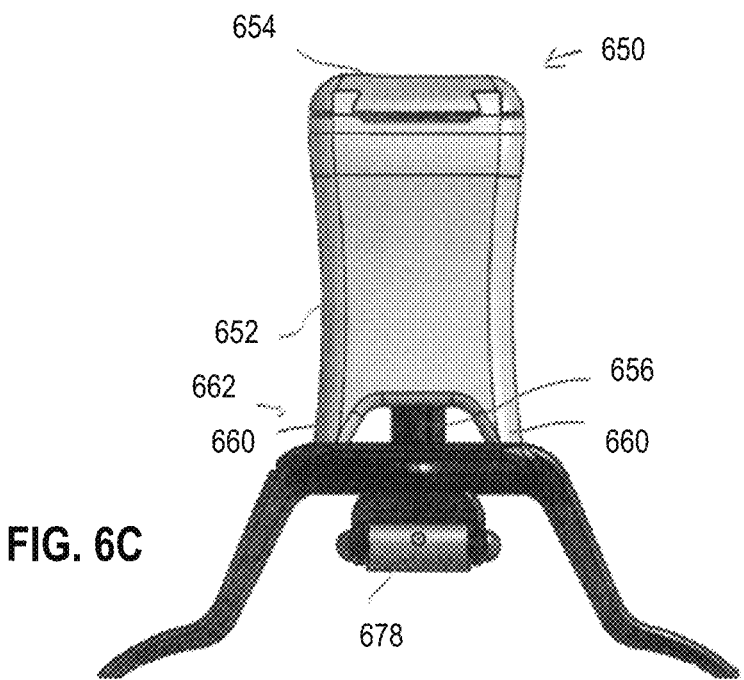
FIG. 6C

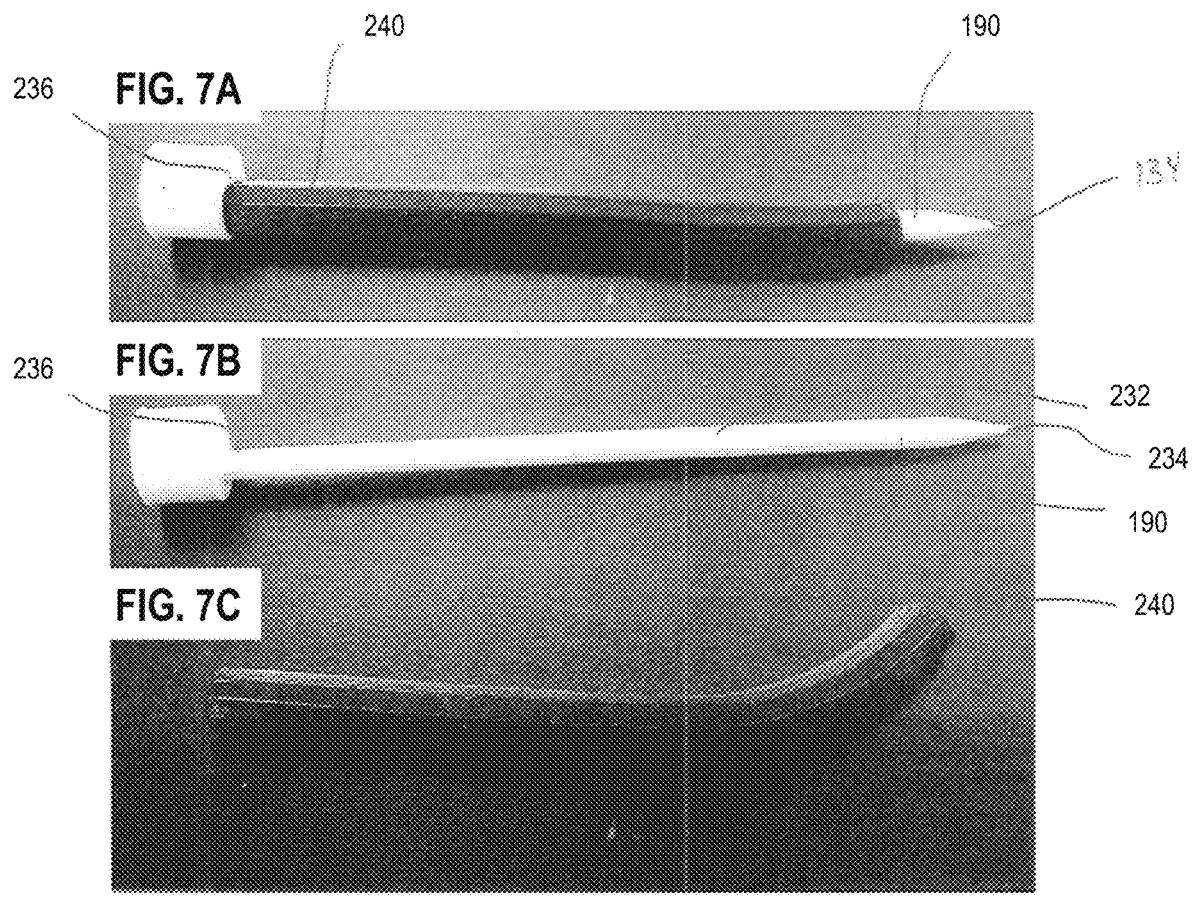

SYSTEM AND METHOD FOR AUTOMATIC EMERGENCY AIRWAY DETECTION

CROSS-REFERENCE TO RELATED APPLICATIONS

This application claims benefit of Provisional Application 62/776,614, filed Dec. 7, 2018 and Provisional Application 62/915,244 filed Oct. 15, 2019, the entire contents of both are hereby incorporated by reference as if fully set forth herein, under 35 U.S.C. § 119(e).

STATEMENT OF GOVERNMENTAL INTEREST

This invention was made with government support under Contract No. W81XWH-19-C-0030 awarded by the United States Army Medical Research and Material Command. The government has certain rights in the invention.

BACKGROUND

Airway compromise is the third leading cause of preventable death in combat casualty care [1]. Accessing a failed airway in emergency situations requires a skilled surgical procedure called a cricothyroidotomy (CT). This procedure is preferable to other methods such as endotracheal intubation in pre-hospital environments because it requires less training, can be performed without sedating the patient, and has lower associated risks than tracheostomies. Unfortunately, this procedure has a low success rate in pre-hospital settings largely due to an inability to locate the cricothyroid membrane using the standard, subjective palpation process [2]. An Emergency Resuscitation (EO2) device will treat patients suffering from an airway obstruction under emergency conditions by creating an artificial airway and providing oxygen to prevent brain death. If performed within three minutes of oxygen deprivation, intrabronchial oxygenation provided by the EO2 can sustain life and delay brain death for up to 30 minutes [3,4].

SUMMARY

A cricothyrotomy is an incision through the cricothyroid membrane of a patient's neck, between the cricoid and thyroid cartilages just above the trachea; and, is considered simpler and less invasive than an incision through the trachea (tracheotomy) in an emergency situation and to have fewer complications. Cricothyrotomy with positive pressure ventilation is often necessary to secure the airway in injuries requiring emergent pulmonary resuscitation when standard intubation methods fail. Particularly when there is an obstruction in the airway or facial trauma rendering endotracheal intubation impossible, an immediate solution is to insert a tube through a hole in the cricothyroid membrane. In some cases, the cricothyrotomy will allow the patient to breathe on their own. In other instances, the cricothyrotomy will provide an entry way for assisted ventilation and/or drug delivery.

It is here recognized that conventional devices used to perform the cricothyrotomy have several drawbacks. For example, conventional devices typically rely on the user to manually locate the cricothyroid membrane, manually mark the cricothyroid membrane and/or manually incise the cricothyroid membrane to provide the entry way for assisted ventilation. It is here noted that even though some of the conventional devices assist the user in manually locating the cricothyroid membrane, the user is still ultimately relied on to manually locate the cricothyroid membrane. Since users of these conventional devices are routinely not medical practitioners, this can result in error in locating the cricothyroid membrane. Thus, the embodiments described herein were developed to automate the cricothyroidotomy procedure, including scanning the neck for a profile and automatically locating the cricothyroid membrane (CTM). In some embodiments, the device or method uses a machine learning algorithms (MLA) to locate the CTM and, incises the membrane using a trocar with a sheath mounted on it, and/or inserts an oxygen catheter.

In a first embodiment, an apparatus includes a frame with a carriage guide. The frame is configured to be secured around a neck of a subject. The apparatus also includes a carriage including a sensor, where the carriage is configured to move along the carriage guide and where the sensor is configured to measure a value of a parameter indicating a topography of the neck of the subject. The apparatus also includes a processor communicatively coupled with the sensor. The apparatus also includes a memory including one or more sequences of instructions. The memory and the one or more sequences of instructions are configured to, with the processor, cause the apparatus to receive first data from the sensor of the value of the parameter indicating the topography of the neck of the subject as the carriage is moved along the carriage guide. The memory and the one or more sequences of instructions are configured to, with the processor, cause the apparatus to determine, with the first data, second data indicating a position along the carriage guide corresponding to the cricothyroid region of the neck. The memory and the one or more sequences of instructions are configured to, with the processor, cause the apparatus to transmit a first signal indicating the second data.

In a second embodiment, a method is provided that includes securing, with an attachment, a frame around a neck of a subject. The frame includes a carriage guide. The method also includes moving a carriage along the carriage guide. The method also includes measuring, with a sensor of the carriage, a value of a parameter indicating a topography of the neck of the subject as the carriage moves along the carriage guide. The method also includes automatically receiving, at a processor, first data from the sensor indicating the topography of the neck of the subject as the carriage moves along the carriage guide. The method also includes automatically determining, with the processor, second data based on the first data, where the second data indicates a position along the carriage guide corresponding to the cricothyroid region of the neck. The method also includes transmitting, with the processor, a first signal indicating the second data.

In a third embodiment, a non-transitory computer-readable medium is provided carrying one or more sequences of instructions. Execution of the one or more sequences of instructions by one or more processors causes the one or more processors to perform the steps of: receiving first data including a value of a parameter indicating a topography of a neck of a subject over a range of the neck; determining second data indicating a position along the range of the neck corresponding to the cricothyroid region of the neck based on the first data; and transmitting a first signal indicating the second data.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 4A is a flow diagram that illustrates an example method for automatic emergency airway detection, according to an embodiment;

FIG. 5A through FIG. 5E are schematic diagrams that illustrate different views of an example of a frame of the apparatus of FIG. 1A, according to an embodiment;

FIG. 6A through FIG. 6C are schematic diagrams that illustrate different views of an example of a roller sensor of the apparatus of FIG. 1A, according to an embodiment;

FIG. 7A through FIG. 7C are schematic diagrams that illustrate side views of an example of a trocar of the apparatus of FIG. 1A, according to an embodiment;

DETAILED DESCRIPTION

A method, system and apparatus are described for automatic emergency airway detection. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5x to 2x, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of determining a location of the cricothyroid membrane for purposes of performing a cricothyrotomy. However, the invention is not limited to this context. In other embodiments, the apparatus or system is used in the context of detection of the correct intercostal space to perform a thoracostomy. In yet other embodiments, the apparatus or system is used in the context of performing a lumbar puncture or similar procedure.

1. OVERVIEW

Figure 1A:
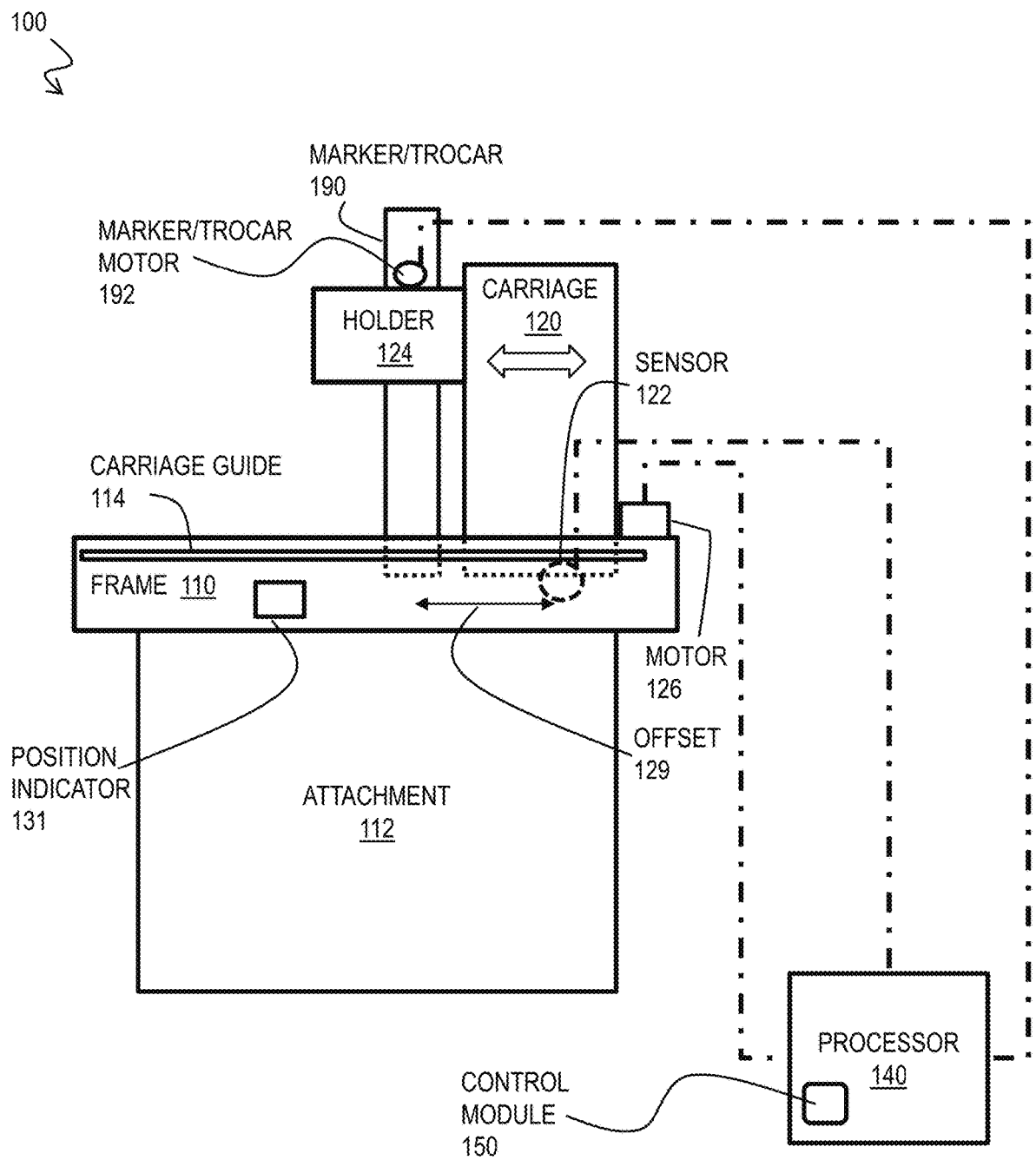
FIG. 1A is a block diagram that illustrates an example of an apparatus for automatic emergency airway detection, according to an embodiment.

FIG. 1A is a block diagram that illustrates an example apparatus 100 for automatic emergency airway detection, according to an embodiment. In this embodiment, the apparatus 100 includes a frame 110 that is configured to be secured around a neck of a subject. In an example embodiment, the frame 110 is shaped so to accommodate the neck of the subject. In one embodiment, the frame 110 includes an attachment 112 that secures the frame 110 around the neck of the subject. In an example embodiment, the attachment 112 is a strap.

In an embodiment, the frame 110 includes a carriage guide 114 and the apparatus 100 includes a carriage 120 that is configured to move along the frame 110 in or on the carriage guide 114. In an example embodiment, the carriage guide 114 is one or more openings defined by the frame 110 or comprises one or more rails. In one embodiment, the carriage 120 is slidably received within the carriage guide 114. In an example embodiment, the carriage guide 114 extends along a range that is sufficient to cover a length of the neck including one or more anatomical features of the neck (e.g. sternal notch, cricothyroid membrane, cricoid cartilage, thyroid cartilage).

In one embodiment, the apparatus 100 includes a motor 126 operatively coupled to the carriage 120, where the motor 126 is configured to cause the carriage 120 to move along the carriage guide 114. In an example embodiment, the motor 126 is communicatively coupled to a processor 140 and upon receiving a signal from the processor 140, the motor 126 automatically causes the carriage 120 to move along the carriage guide 114. In one example embodiment, upon receiving the signal from the processor 140, the motor 126 automatically causes the carriage 120 to move incremental distances (e.g. move an incremental distance, stop for incremental time period, move another incremental distance, stop, etc.) along the carriage guide 114.

In another embodiment, the apparatus 100 excludes the motor 126 (or the motor 126 is not activated) and the carriage 120 can be manually moved along the carriage guide 114 (e.g. by a user physically moving the carriage along the carriage guide 114).

In an embodiment, the apparatus 100 includes a sensor 122 that is configured to measure a value of a parameter indicating a topography of the neck of the subject. In one embodiment, the sensor 122 is connected to or integrated within the carriage 120 so that the sensor 122 moves with the carriage 120 along the carriage guide 114. In one example embodiment, the parameter indicating the topography is a height of the neck surface measured in a direction orthogonal to a direction of movement along the carriage guide 114.

Figure 11:
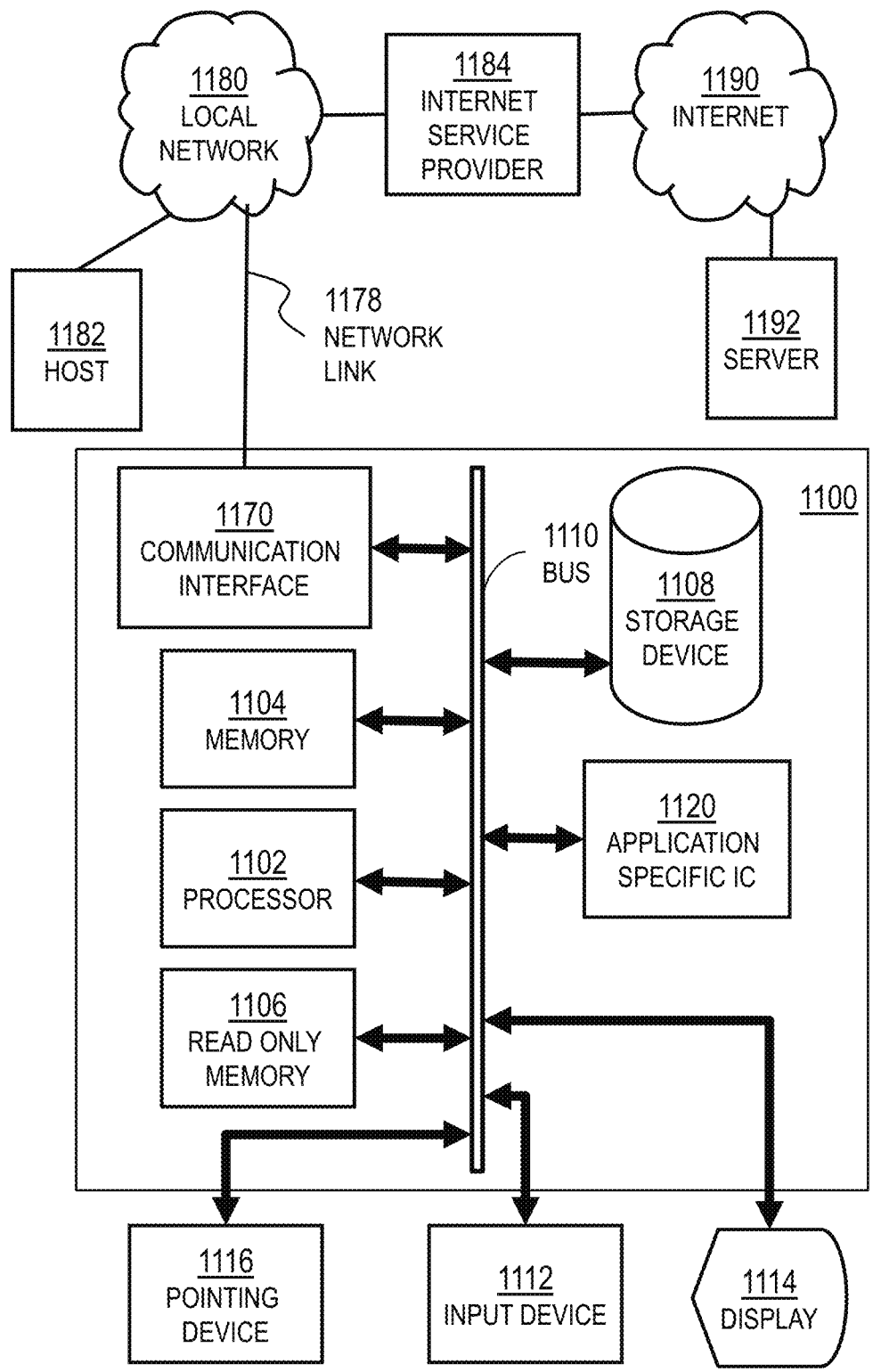
FIG. 11 is a block diagram that illustrates a computer system upon which an embodiment of the invention may be implemented.
Figure 12:
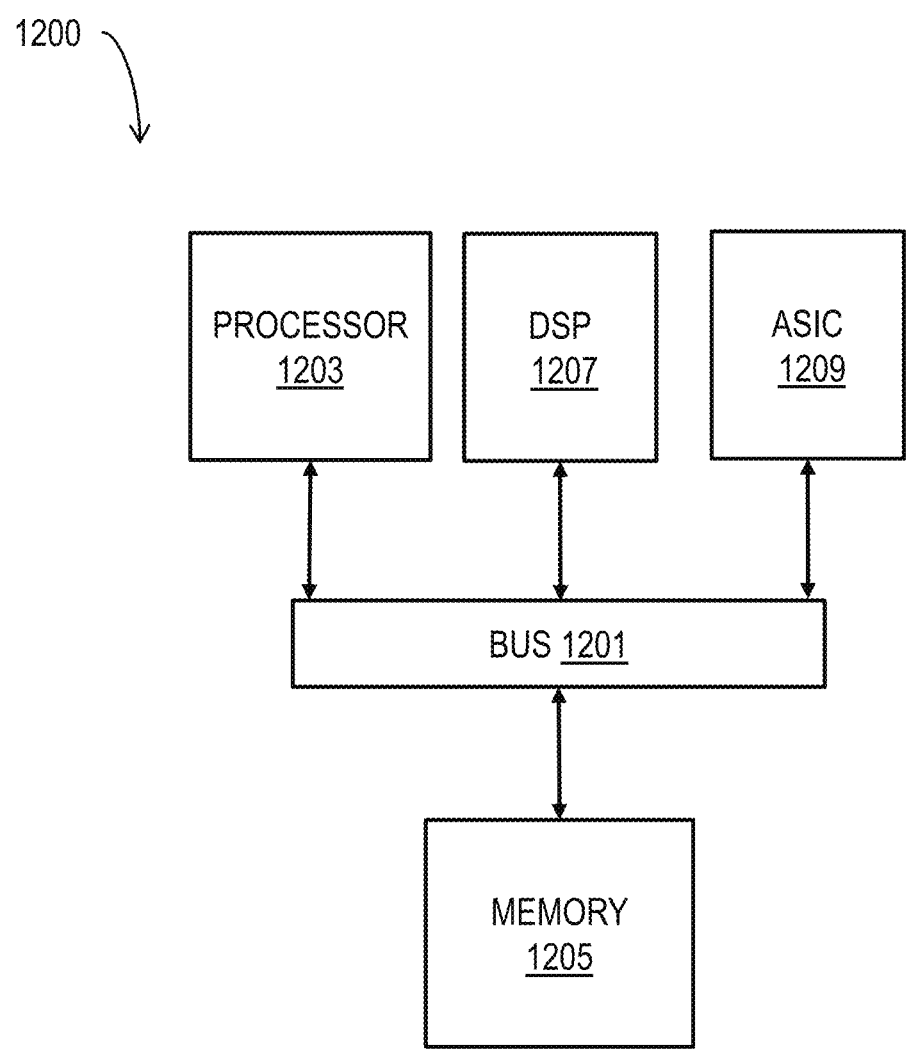
FIG. 12 is a block diagram that illustrates a chip set upon which an embodiment of the invention may be implemented.

In an embodiment, the apparatus 100 includes the processor 140 that is communicatively coupled to the sensor 122 by wired or wireless communication links or some combination. In one embodiment, the processor 140 receives first data from the sensor 122 of the value of the parameter indicating the topography of the neck, as the carriage 120 is moved along the carriage guide 114. The processor 140 includes an optimized control module 150 to perform one or more steps of a method described below with reference to FIG. 4A and/or a method described below with reference to FIG. 4B. In various embodiments, the processor 140 comprises one or more general purpose computer systems, as depicted in FIG. 11 or one or more chip sets as depicted in FIG. 12, and instructions to cause the computer or chip set to perform one or more steps of a method described below with reference to FIG. 4A or FIG. 4B.

In an embodiment, the apparatus 100 includes a holder 124 connected to the carriage 120 so that the holder 124 moves with the carriage 120 along the carriage guide 114. In an embodiment, the holder 124 is configured to removably hold a marker or a trocar 190. In an example embodiment, the marker 190 is removably held by the holder 124 when the apparatus 100 is used to mark (but not insert through) the cricothyroid membrane of the neck. In this example embodiment, the apparatus 100 is used to mark the cricothyroid membrane and the trocar 190 (or a trocar separate from the apparatus 100) can be manually inserted through the cricothyroid membrane after its location is marked on the neck of the subject by the marker 190. In another example embodiment, the trocar 190 is removably held by the holder 124 when the apparatus 100 is to be used to insert the trocar into (and not merely mark) the cricothyroid membrane of the neck.

In an embodiment, when the trocar 190 is disposed in the holder 124, the trocar 190 includes a handle (not shown) that is configured to allow a user to manually insert the trocar through the cricothyroid membrane of the neck when properly located. In another embodiment, the apparatus 100 includes a position indicator 131 that indicates a location of the trocar 190 along the carriage guide 114 as the user manually moves the trocar 190 (e.g. with the handle) along the carriage guide 114. In this embodiment, the position indicator 131 conveniently provides the user with notice when the trocar is positioned at the actual location of the target (e.g. the cricothyroid membrane).

In an embodiment, the apparatus 100 includes a motor 192 for the marker or trocar 190. In an example embodiment, the motor 192 is communicatively coupled with the processor 140 and upon receiving a signal from the processor 140, the motor 192 automatically causes the marker 190 to mark the cricothyroid membrane (e.g. with incandescent ink that glows under low light conditions). In another example embodiment, upon receiving the signal from the processor 140, the motor 192 automatically causes the trocar 192 to be inserted (e.g., to penetrate) through the cricothyroid membrane. In one embodiment, the motor 192 is connected to the trocar 190 to cause the trocar 190 to be inserted (e.g., to penetrate) through the cricothyroid membrane.

In an embodiment, a system includes the trocar 190 in the holder 124 and the motor 126 that is connected to the carriage 120 and causes the carriage 120 to move along the carriage guide 114 in a first direction (e.g. horizontal direction in FIG. 1A). In one embodiment, the apparatus 100 also includes a linear sensor (e.g. rotary encoder of the motor 126) that measures movement of the carriage 120 along the carriage guide 114 in the first direction. In this example embodiment, data indicating the movement of the carriage 120 along the carriage guide 114 is transmitted from the linear sensor to the processor 140. In another embodiment, the apparatus 100 includes the motor 192 that is connected to the trocar 190 and is configured to cause the trocar 190 to be inserted through the cricothyroid membrane. In another embodiment, the apparatus 100 includes a linear sensor (e.g. rotary encoder of the motor 192) that measures movement of the trocar 190 in a second direction (e.g. vertical direction in FIG. 1A) orthogonal to the first direction. In this example embodiment, data indicating the movement of the trocar 190 in the second direction is transmitted from the linear sensor to the processor 140.

In another embodiment, a system includes the marker 190 in the holder 124 and the motor 126 that is connected to the carriage 120 and causes the carriage 120 to move along the carriage guide 114 in a first direction (e.g. horizontal direction in FIG. 1A). In one embodiment, the apparatus 100 also includes a linear sensor (e.g. rotary encoder of the motor 126) that measures movement of the carriage 120 along the carriage guide 114 in the first direction. In this example embodiment, data indicating the movement of the carriage 120 along the carriage guide 114 is transmitted from the linear sensor to the processor 140. In another embodiment, the apparatus 100 includes the motor 192 that is connected to the marker 190 and is configured to cause the marker 190 to mark the cricothyroid membrane. In another embodiment, the apparatus 100 includes a linear sensor (e.g. rotary encoder of the motor 192) that measures movement of the marker 190 in a second direction (e.g. vertical direction in FIG. 1A) orthogonal to the first direction. In this example embodiment, data indicating the movement of the marker 190 in the second direction is transmitted from the linear sensor to the processor 140.

Figure 1B:
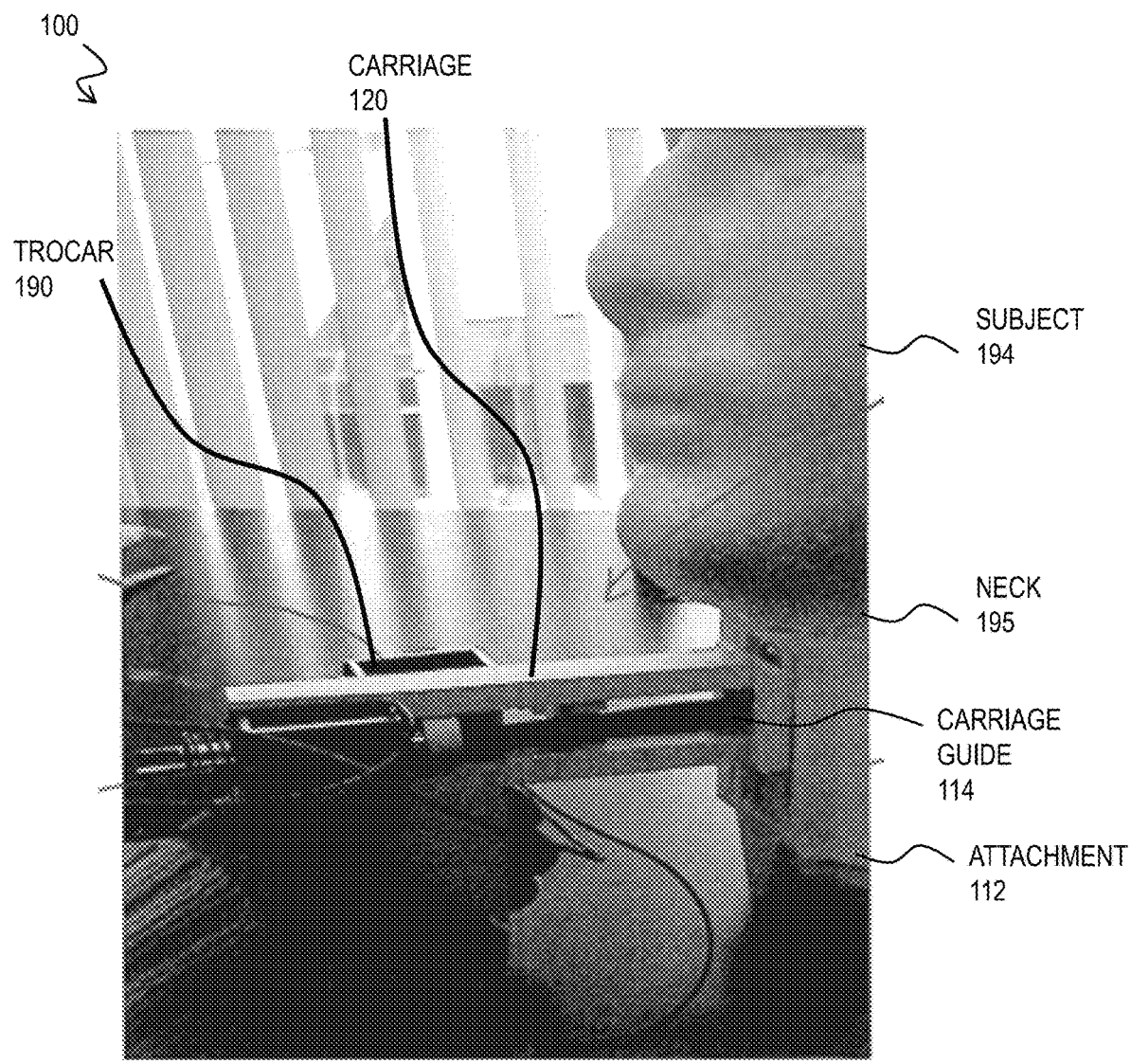
FIG. 1B is an image that illustrates an example of the apparatus of FIG. 1A secured around a neck of a subject, according to an embodiment.

FIG. 1B is an image that illustrates an example of the apparatus 100 of FIG. 1A secured around a neck of a subject, according to an embodiment. In an embodiment, the frame 110 is secured around the neck 195 of the subject 194 using the attachment 112 which is a strap. In one embodiment, the strap secures the frame 110 around the neck 195 of the subject 194 using any fastener known by one of ordinary skill in the art (e.g. hook and loop fasteners). In an embodiment, the frame 110 is secured around the neck 195 of the subject 194 so that the carriage guide 114 aligns with a region of the neck 195 corresponding with one or more anatomical regions of the neck (e.g. sternal notch, cricothyroid membrane, cricoid cartilage, thyroid cartilage, etc.). In an example embodiment, the frame 110 is positioned so that a base of the frame 110 is secured in the sternal notch of the neck 195 and so that the carriage guide 114 extends over a region of the neck 195 that encompasses the cricothyroid region.

Figure 4B:
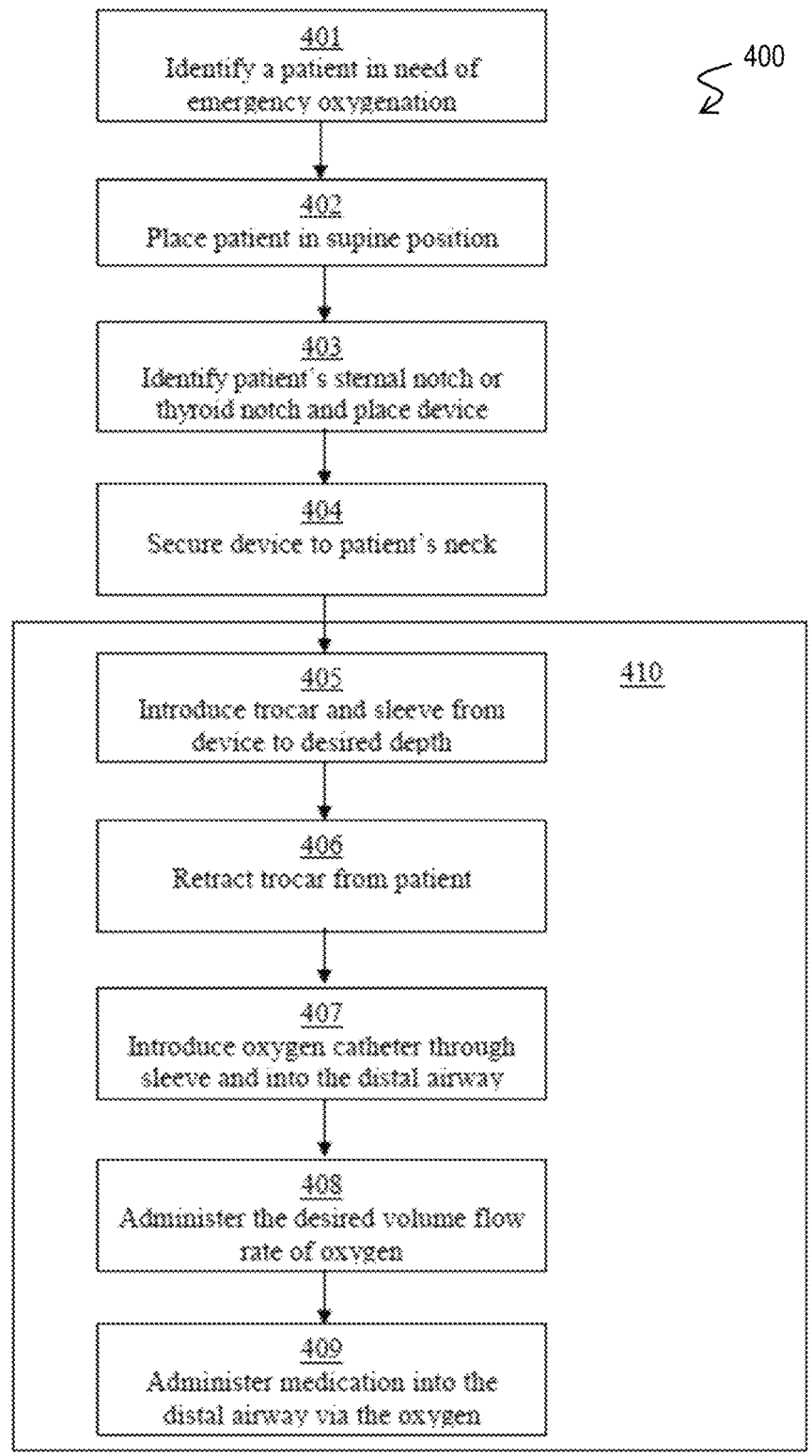
FIG. 4B is a flow diagram that illustrates an example method for providing a flow of oxygen to an airway of a subject, according to an embodiment.

FIG. 4A is a flow diagram that illustrates an example method 450 for automatic emergency airway detection, according to an embodiment. Although steps are depicted in FIG. 4A, and in subsequent flowchart FIG. 4B, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In an embodiment, step 451 includes securing the frame 110 around the neck 195 of the subject 194 with the attachment 112. In one embodiment, in step 451 the attachment 112 is a strap that is used to secure the frame 110 around the neck 195 of the subject 194 so that the frame 110 is rigidly secured around the neck 195. In an embodiment, in step 451 the frame 110 is secured to the neck 195 of the subject 194 so that the carriage guide 114 overlaps with various anatomical regions of the neck 195 (e.g. sternal notch, cricothyroid membrane, cricoid cartilage, thyroid cartilage, etc.). In an embodiment, in step 451 the frame 110 is secured to the neck 195 so that the carriage guide 114 overlaps with an entire width of the trachea and an additional distance (e.g. about 2 inches or in a range from about 1 inch to about 3 inches) on one or both sides of the trachea for lateral support to prevent shifting.

In step 453, the carriage 120 is moved along the carriage guide 114 of the frame 110. In one embodiment, step 453 involves the motor 126 automatically moving the carriage 120 along the carriage guide 114 upon receiving a signal from the processor 140. In another embodiment, step 453 involves the user manually moving the carriage 126 (e.g. using the handle) along the carriage guide 114. In an example embodiment, in step 453 the carriage 120 is moved at incremental distances (e.g. about 1 millimeters (mm) or in a range from about 0.1 mm to about 2 mm) over a range of the neck 195 that corresponds to the length of the carriage guide 114 (e.g. about 80 mm or in a range from about 50 mm to about 120 mm).

In step 455, the sensor 122 measures the value of the parameter that indicates the topography of the neck 195 of the subject 194, as the carriage 120 moves in step 453. In one embodiment, the parameter is a height of the neck 195 surface in a direction orthogonal to the carriage guide 114. In one embodiment, before the carriage 120 is moved in step 453 the apparatus 100 is initiated so that the sensor 122 commences to measure the value of the parameter indicating the topography of the neck 195. In an example embodiment, the apparatus 100 is initiated by the user interacting with one or more input devices 1112 (FIG. 11) of the processor 140. In an embodiment, in step 455 the sensor 122 measures the value of the parameter that indicates the topography of the neck 195 over various anatomical regions of the neck including one or more of the sternal notch, the cricoid cartilage, the cricothyroid membrane, thyroid cartilage).

In step 457, the processor 140 receives first data from the sensor 122 of the values of the measured parameter during step 455 as the carriage 120 moved along the carriage guide 114. In one embodiment, the processor 140 stores the first data in a memory of the processor 140. In another embodiment, the processor 140 stores in the memory a value for an offset 129 between the sensor 122 and the marker 190 or trocar 190.

In step 459, the processor 140 automatically determines second data based on the first data, where the second data indicates a position along the carriage guide 114 corresponding to the cricothyroid membrane. In one embodiment, in step 459 the processor 140 uses one or more criteria of the first data to determine the second data. In an example embodiment, in step 459 the processor 140 assesses the first data to identify a first region (e.g. cricoid cartilage region 1006 depicted in FIG. 10A, described in more detail below, with the parameter values having a first value), a second region (e.g. thyroid cartilage region 1008 depicted in FIG. 10A with the parameter values having a second value greater than the first value) and a third region between the first region and second region (e.g. cricothyroid membrane 1010 depicted in FIG. 10A with the parameter values less than the first value and the second value). In this example embodiment, the processor 140 determines the second data based on the third region. In an example embodiment, the processor 140 determines the second data based on other criteria such as one or more of the fourteen criteria (1)-(14) discussed in more detail below with respect to FIG. 10B.

In step 461, the processor 140 transmits a signal indicating the second data determined in step 459. In one embodiment, in step 461 the processor 140 transmits the signal to the motor 126 which subsequently automatically moves the carriage 120 along the carriage guide 114 so that the trocar 190 or marker 190 are aligned with the position along the carriage guide 114 corresponding to the cricothyroid membrane 1010. In an embodiment, the processor 140 uses the stored value of the offset 129 in the memory to determine the second data, to ensure that the trocar 190 or marker 190, rather than the carriage 120 is aligned with the position along the carriage guide 114 corresponding to the cricothyroid membrane. In another embodiment, after the motor 126 automatically moved the carriage 120 so that the trocar 190 or marker 190 is aligned with the cricothyroid membrane 1010, in one embodiment the processor 140 transmits a signal to the motor 192 to automatically cause the trocar 190 to be inserted through the cricothyroid membrane (or automatically cause the marker 190 to mark the cricothyroid membrane). In still other embodiments, after the motor 126 automatically moves the carriage 120 so that the trocar 190 or marker 190 is aligned with the cricothyroid membrane, the user can manually insert the trocar 190 (using the handle) through the cricothyroid membrane or can manually move the marker 190 (using the handle) to mark the skin location corresponding to the cricothyroid membrane. After manually marking the skin location corresponding to the cricothyroid membrane, the user can then manually insert the trocar 190 (or a trocar that is not part of the apparatus 100) through the cricothyroid membrane, using the mark on the skin corresponding to the cricothyroid membrane to ensure an accurate insertion.

In one embodiment, in step 461 the processor 140 transmits the signal to a display (e.g. display 1114 of FIG. 11) of the processor 140 so to communicate to the user the position along the carriage guide 114 corresponding to the cricothyroid membrane. In an embodiment, the user can then use this position and manually move the carriage 120 along the carriage guide 114 (e.g. using the position indicator 131 that indicates the actual location of the marker 190 or trocar 190 along the carriage guide 114) so that the trocar 190 or marker 190 are aligned with the position along the carriage guide 114 corresponding to the cricothyroid membrane. After the user manually moved the carriage 120 so that the trocar 190 or marker 190 is aligned with the cricothyroid membrane, in one embodiment the processor 140 transmits a signal to the motor 192 to automatically cause the trocar 190 to insert through the cricothyroid membrane (or automatically cause the marker 190 to mark the cricothyroid membrane). In still other embodiments, after the user manually moved the carriage 120 so that the trocar 190 or marker 190 is aligned with the cricothyroid membrane, the user can manually insert the trocar 190 (using the handle) through the cricothyroid membrane or can manually move the marker 190 (using the handle) to mark the cricothyroid membrane. After manually marking the cricothyroid membrane, the user can then manually insert the trocar 190 (or a trocar that is not a part of the apparatus 100) through the cricothyroid membrane, using the mark on the cricothyroid membrane to ensure an accurate insertion.

2. EXAMPLE EMBODIMENTS

FIG. 2A through FIG. 2D are schematic diagrams that illustrate example stages of insertion of a trocar, sleeve and oxygen catheter into an airway of the neck in FIG. 1B, according to an embodiment. In an embodiment, the motor 192 is configured to automatically insert the trocar 190 and a sheath or sleeve 240 partially covering the trocar 190 through the cricothyroid membrane into a distal airway of the neck, withdraw the trocar 190, and/or further insert the catheter 210 into the distal airway of the neck. In this embodiment, the apparatus 100 inserts the trocar 190 and sleeve 240 into the distal airway of the neck and further removes the trocar 190. In the illustrated embodiment, the sleeve curves downward when the trocar is removed, e.g., due to material memory, as described in previous work by some inventors. In yet another embodiment, the apparatus 100 further advances the oxygen catheter 210 into the distal airway of the neck. In still yet another embodiment, the apparatus 100 automatically inserts the trocar 190, sleeve 240, and/or oxygen catheter 210. In another embodiment, the user can use the handle of the trocar 190 to manually insert the trocar 190 and sleeve 240 through the cricothyroid membrane.

Figure 2A:
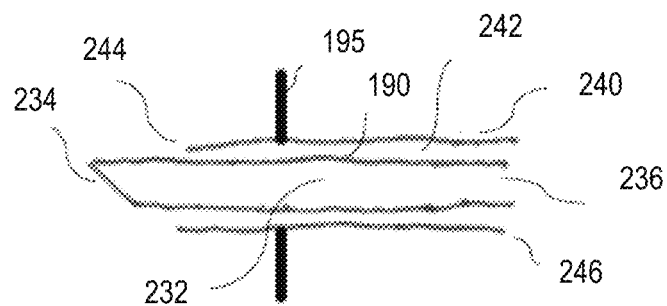
FIGS. 2A through FIG. 2D are schematic diagrams that illustrate example stages of insertion of a trocar, sleeve and oxygen catheter into an airway of the neck in FIG. 1B, according to an embodiment.

FIG. 2A depicts the trocar 190 with an elongated body 232 including a distal tip 234 and a proximal end 236. In an embodiment, the distal tip 234 is configured to penetrate through the skin of the neck and the cricothyroid membrane (e.g. the distal tip 234 is generally sharp). In another embodiment, the distal tip 234 of trocar 190 is inserted a predetermined distance into the distal airway of the neck. In other embodiments, the apparatus 100 is configured to insert the distal tip 234 of the trocar 190 an optimal or preferred distance. In an example embodiment, the apparatus 100 includes one or more pressure sensors located on the distal tip 234 that can measure an insertion force required to overcome the resistance of inserting the trocar 190 through the skin and cricothyroid membrane. In this example embodiment, the pressure sensors will generally measure a higher insertion force when the distal tip 234 is initially penetrating the skin and/or cricothyroid membrane compared to when the distal tip 234 is through the cricothyroid membrane and in the distal airway. The sensor will then detect increased pressure when the tip makes contact with the distal wall of the airway; and, the increase will signal that the trocar should not be advanced any further.

Figure 2B:
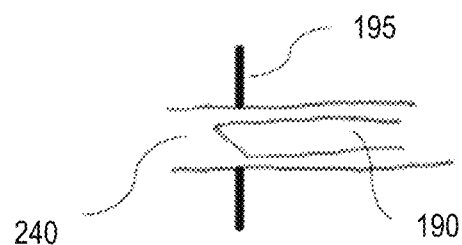
Figure 2C:
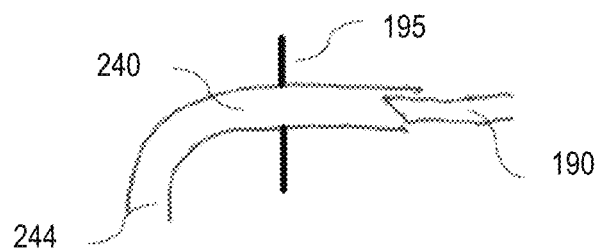

In an embodiment, the sleeve 240 is configured to cover at least a portion of the trocar 190 and is further configured to enter the subject as the trocar 190 is advanced into the distal airway of the neck. As depicted in FIG. 2A through FIG. 2D, the sleeve 240 includes an elongated cylindrical-like body 242 having a distal end 244 and a proximal end 246. The neck 195 of the subject is also depicted and the trocar 190 and sleeve 240 are being inserted through the neck 195 of the subject (e.g. the cricothyroid membrane). In an embodiment, FIG. 2B shows the trocar 190 being removed from the sleeve. In this embodiment, the sleeve 240 remains in position in the distal airway of the neck 195 as the trocar 190 is removed. In another embodiment, FIG. 2C shows the sleeve 240 fully inserted into the distal airway of the neck 195. As shown in FIGS. 2A through FIG. 2D, the sleeve 240 may be bent or configured to have a natural bend when the trocar 190 is removed so that the sleeve distal end 244 points inferiorly towards the lungs of the subject to safely pass the oxygen catheter 210 into the distal airway of the subject. In certain embodiments, the sleeve 240 is made of shape memory material, such as Nitinol. In another embodiment the outer surface of sleeve 240 is configured to be held in position within the neck 195 of the subject, for example by increasing friction between the sleeve 240 and the neck 195 by having a roughened surface.

Figure 2D:
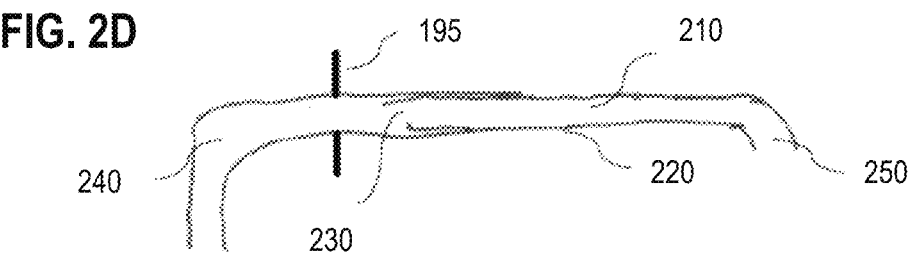

In an embodiment, FIG. 2D illustrates the passage of oxygen catheter 210 through the sleeve 240 and into the distal airway. In an embodiment, the oxygen catheter 210 comprises an elongated body 220, a distal end 230 and proximal end 250. In one embodiment, the distal end 230 may have one or more fenestrations at the end to help distribute the oxygen in the distal airway. In this embodiment, the distal end 230 may also be configured to separate into two or more oxygen catheters to allow for the passage into two or more branches of the lungs. The distal end 230 may also be soft to reduce the possibility of damage to the lungs as it is inserted. In an embodiment, a catheter proximal end 250 is configured to be in fluid communicate with an oxygen source. In one embodiment, the oxygen source is a portable canister of compressed oxygen with a pressure regulator.

Figure 3A:
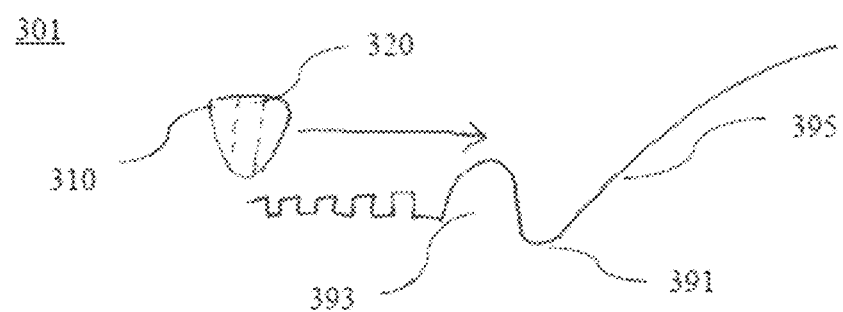
FIG. 3A is a schematic diagram that illustrates an example of a bumper sensor of the apparatus of FIG. 1A, according to an embodiment.
Figure 3B:
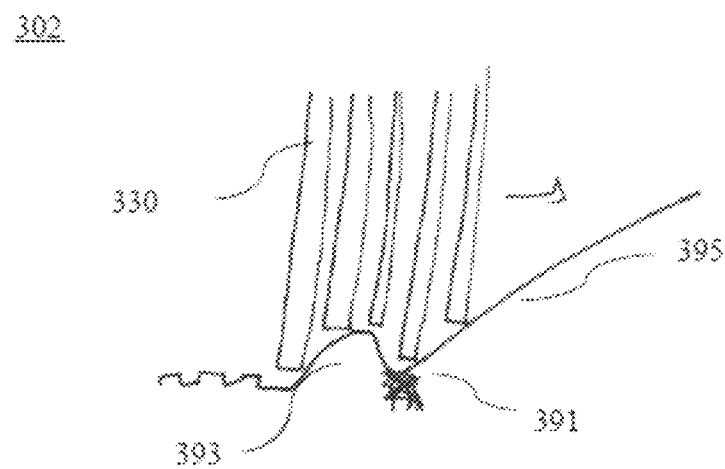
FIG. 3B is a schematic diagram that illustrates an example of a set of sensor pins of the apparatus of FIG. 1A, according to an embodiment.

FIG. 3A is a schematic diagram that illustrates an example of a bumper sensor of the apparatus 100 of FIG. 1A, according to an embodiment. FIG. 3B is a schematic diagram that illustrates an example of a set of sensor pins of the apparatus 100 of FIG. 1A, according to an embodiment. FIG. 3A and FIG. 3B illustrate two examples of the sensor 122 of the apparatus 100. In an embodiment, FIG. 3A illustrates the bumper sensor 301 which attaches to a distal end of the apparatus 100. In one embodiment, the bumper sensor 301 has an elongated member 310 and a central channel 320 for the passage of the trocar 190 and oxygen catheter 210. The cricothyroid membrane 391 is a soft recessed region of the neck which is situated between the cricoid cartilage 393 and the thyroid cartilage 395. The patient anatomy is topographically identified and assigned identification numbers for illustrative purposes and are not elements of the invention. In this example embodiment, the user is able to identify the cricothyroid membrane 391 by placing bumper sensor 301 on the base of the neck (e.g., sternal notch). As the bumper sensor 301 is manually or automatically moved up the neck, it will naturally settle into the recess where the cricothyroid membrane 391 is located. This natural settling indicates to the user that the apparatus 100 is properly located (e.g. that the trocar 190 passed through the channel 320 is aligned with the cricothyroid membrane). In one embodiment, the bumper sensor 301 is (manually or automatically) moved along the carriage guide 114 and the position of the cricothyroid membrane is located by observing the location where the bumper sensor 301 naturally settles.

FIG. 3B illustrates a linear position sensor set 302 that also includes a central cavity to allow the passage of trocar 190 and oxygen catheter 210. In one embodiment of the apparatus 100, the linear position sensor 302 is placed at the base of the patient's neck (e.g. sternal notch). As the apparatus 100 translates along the patient's neck, the pins 330 will adjust up and down along the topography of the patient's neck. In an example embodiment, the pins 330 are positioned in the carriage guide 114 and moved along the surface of the neck 195 along with the carriage 120. In certain automated embodiments, when certain topographic parameters are met, the apparatus 100 will trigger the trocar insertion process and/or other subsequent events. In other manual embodiments, the user will know when the apparatus 100 is in position when one or more pins 330 settle in the recess of the cricothyroid membrane. In these embodiments, the user is manually moving the carriage 120 with the pins 330 along the carriage guide 114 and may determine the location of the cricothyroid membrane along the carriage guide 114 based on observing the settling of the pins 330.

FIG. 4B is a flow diagram that illustrates an example of a method 400 for providing a flow of oxygen to an airway of a subject, according to an embodiment. In an embodiment, step 401 includes identifying a patient that is in need of emergency oxygenation. In step 402, the patient is placed in a supine position. Although some embodiments may omit step 402, doing so helps steady the patient and assists with the proper placement of the apparatus 100. In step 403, the patient's sternal notch or thyroid notch is identified. In one embodiment, a trained user can identify the notches by touch.

In step 404 the apparatus 100 is secured to the patient's neck, which can be optional in some embodiments. In an embodiment, step 404 is similar to step 451. In some embodiments, between step 404 and 405, one or more steps of the method 450 are performed. In step 405, the trocar 190 and sleeve 240 are inserted using the motor 192 (or manually using the handle) through the patient's skin and cricothyroid membrane until the distal tip 234 of the trocar 190 enters the airway. The trocar 190 and sleeve 240 may enter a predetermined fixed distance or a sensor on the device may advance the assembly an optimal distance. Step 406 includes removing the trocar 190 from the patient.

In step 407 the oxygen catheter 210 is inserted in the sleeve 240 into the lungs of the patient. In certain embodiments where a multi-lumen catheter is used, the individual ends may enter different branches of the distal airway. In certain embodiments, the oxygen catheter 210 is advanced a fixed distance. In other embodiments the apparatus 100 determines the necessary depth. In step 408, oxygen is introduced into the patient at the desired volume flow rate. The volume flow rate may be adjusted by the user depending on the dynamic needs of the patient. In some embodiments, in step 409 medication is introduced into the distal airway through the oxygen catheter 210. In some embodiment, steps 405-409 can be fully or partially automated by the apparatus 100. Such a configuration is depicted in FIG. 4B as step 410.

FIG. 5A through FIG. 5E are schematic diagrams that illustrate different views of an example of a frame of the apparatus of FIG. 1A, according to an embodiment. The frame is a collar 542 that has a central frame with side rails 512, a central opening 514, and wings 516 configured to flushly fit the collar 542 to varied neck anatomies. In the illustrated embodiment, the wings 516 are flexible to accommodate, such as by curving or bending, different patients that have various neck diameters. For example, some patients may have neck larger diameters such that the wings 516 curve or bend to substantially match the diameter of the patient's neck. The wings 516 may be formed of many materials to achieve the desired degree of flexibility. For example, the wings 516 of an example embodiment are formed of plastic, although other materials may be used, such as rubbers, metals, composites, or the like.

In an embodiment, the collar 542 has a side rail 512 on each longitudinal side of the central opening 514. The central opening 514 and side rails 512 are oriented parallel to the patient's neck when the collar 542 is secured; and, are configured to allow and guide movement of the carriage 120 and trocar 190 or marker 190 along the patient's neck. In an embodiment, the side rail 512 and/or the central opening 514 define the carriage guide 114 so that each side rail 512 is configured to slidably couple to the carriage 120 and sensor 122 to guide the sensor 122 as it translates along a patient's neck to locate the cricothyroid membrane. In the illustrated embodiment, each side rail 512 is an anterior-facing groove-like indentation, however, other embodiments may have medial- or lateral-facing side rails or the like. In one embodiment, the carriage 120 and sensor 122 are configured to slidably couple to each of the side rails 512 of the collar 524.

FIG. 6A through FIG. 6C are schematic diagrams that illustrate different views of an example of a roller sensor of the apparatus of FIG. 1A, according to an embodiment. In an embodiment, the roller sensor includes a sensor assembly 650 configured to translate along the patient's neck. In an example embodiment, the sensor assembly 650 includes a handle flange 652, a top cap 654, a shaft assembly 656, and a shaft force sensor (not shown). The handle flange 652 has a pair of legs 660 at a proximal end 662 in which each leg 660 is configured to slidably couple to the collar 542. The handle flange 652 is generally hollow and extends distally from proximal end 662 and the legs 660, which is generally anterior of the patient when the sensor assembly 650 and collar 542 are secured to the patient's neck, for example.

The top cap 654 of the current embodiment is slidably removable to a distal end of the handle flange 652 opposite the pair of legs 660 and is configured to support a force that is transmitted between the patient's neck and the top cap 654 by the shaft assembly 656. The top cap 654 of the current embodiment is slidably removable to the handle flange 652 with dovetail-like grooves, however, other types of attachment may be used, such as fasteners, clips, and the like.

The roller sensor measures the force transmitted by the shaft assembly 656 as it translates along the patient's neck. In this embodiment, the sensor assembly 650 is used as the sensor 122 in the assembly 100 and moves along the carriage guide 114 with the carriage 120. The roller sensor may be a common-type of force sensor used to measure axial forces, such as a stress-strain sensors, capacitive sensors, fiber optic sensors, and the like. In the current embodiment, the roller sensor measures the force transmitted by the shaft assembly 656 and outputs the force measurements to the processor 140, e.g. to a display or indicator of the processor 140. The indicator may be a visual indicator or alert, such as a light or display screen, and/or an auditory indicator, for example. In one embodiment, the indicator displays a graph (e.g. FIG. 10A). Furthermore, the output may be used to automatically control translation of the sensor assembly 656 along the collar 542 to locate the cricothyroid membrane on the patient's neck.

In an embodiment, the shaft assembly 656 is configured to transmit forces from the patient's neck based on a roller 678 passing over the surface of the neck and the roller 678 transmits the various forces to a sensor (not shown) within the sensor assembly 650 through one or more internal components (e.g. spring, spring shaft) within the sensor assembly 650. In an embodiment, the roller 678 is configured to roll along the patient's neck in the direction of translation (e.g. as the carriage 120 moves along the carriage guide 114), and is slidably and frictionally attached to the proximal end of the shaft assembly 656. The roller 678 of the current embodiment includes a horizontal roller that has a rotational axis generally perpendicular to a shaft of the assembly 656.

FIG. 7A through FIG. 7C are schematic diagrams that illustrate side views of an example of a trocar of the apparatus of FIG. 1A, according to an embodiment. In an embodiment, FIG. 7A illustrates an embodiment of the trocar 190 and the sleeve 240 partially covering the trocar 190 prior to inserting the trocar 190 through the cricothyroid membrane (FIG. 2A). FIG. 7A depicts that the trocar 190 has a distal tip 234 which is configured to penetrate the subject's skin and cricothyroid membrane (e.g. generally sharp). In another embodiment, FIG. 7B illustrates the trocar 190 without the sleeve 240 covering the trocar 190. In yet another embodiment, FIG. 7C illustrates the sleeve 240 that is slightly bent toward the distal end 244 to accommodate the sleeve being angled downward in the airway of the neck of the patient after being inserted into the cricothyroid membrane.

Figure 8A:
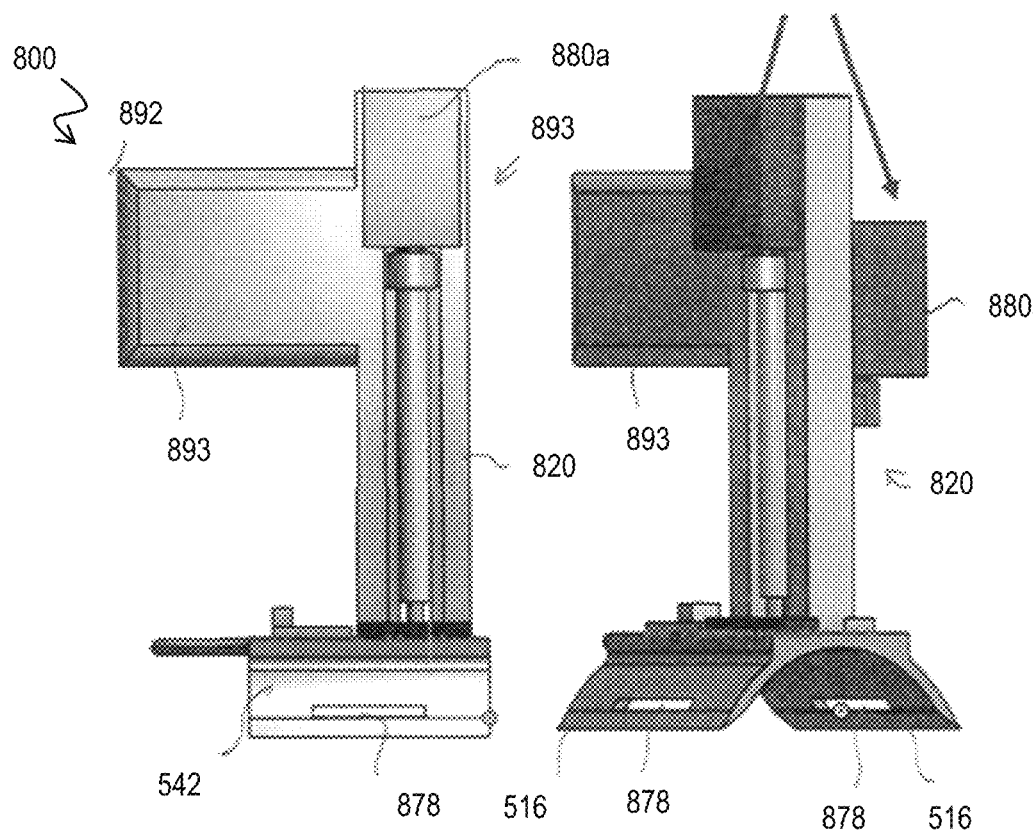
FIG. 8A through FIG. 8C are schematic diagrams that illustrate different views of an example apparatus of FIG. 1A, according to an embodiment.
Figure 8B:
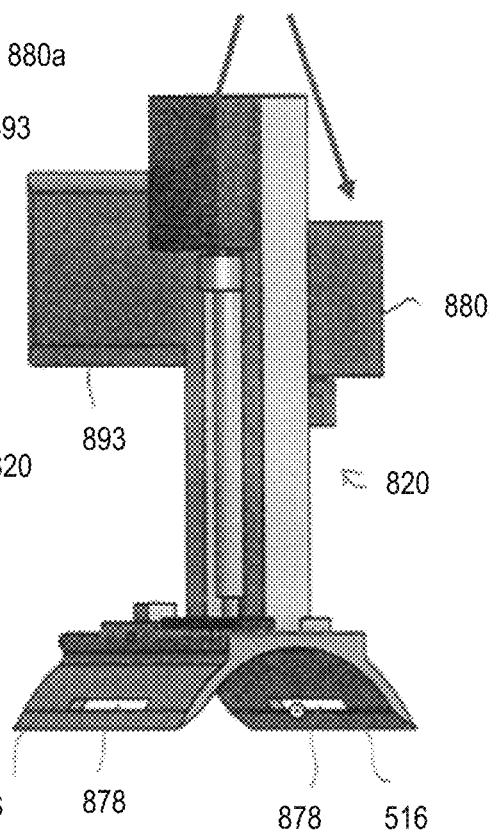
Figure 8C:
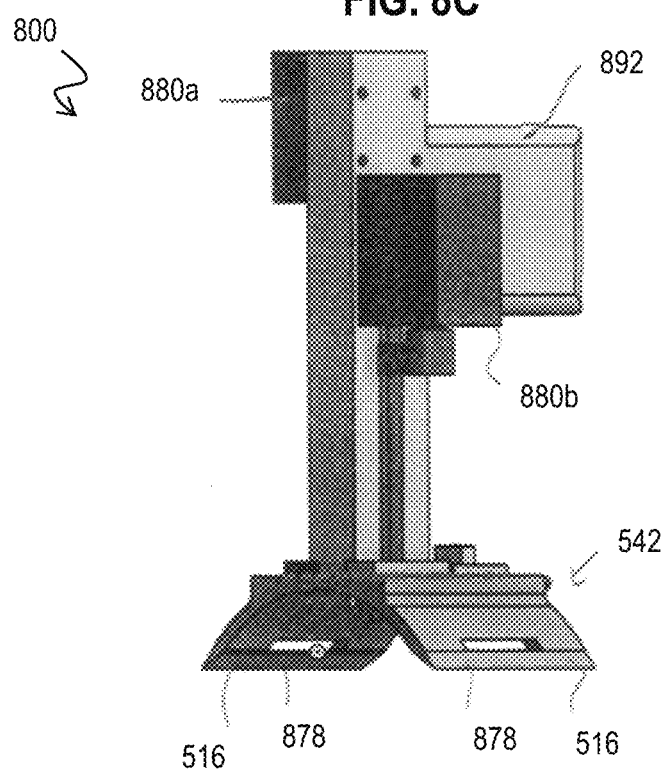

FIG. 8A through FIG. 8C are schematic diagrams that illustrate different views of an example apparatus of FIG. 1A, according to an embodiment. In an embodiment, the apparatus 800 includes the collar 542 to be used as the frame 110. In an embodiment, the apparatus 800 includes a carriage 820 that is configured to move along the side rails 512 and central opening 514 (carriage guide 114 of the frame 110). In one embodiment, the apparatus 800 includes an insertion mechanism 892 that includes one or more solenoids 880a, 880b (trocar motor 192) that are used to automatically insert the trocar 190 through the cricothyroid membrane upon receiving a signal from the processor 140. In yet another embodiment, the apparatus 800 includes a handle 893 that the user can hold to manually insert the trocar 190 through the cricothyroid membrane. In still another embodiment, the collar 542 defines one or more strap openings 878 aligned with the side rails 512 and/or the opening 514 and/or the neck of the subject, so that the straps (attachment 112) can be passed through the strap openings 878 to securely fix the collar 542 around the neck of the subject. In an example embodiment, the first solenoid 880a is coupled to the trocar 190 and thus automatically causes the trocar 190 to insert and retract from the neck 195 of the subject. In an example embodiment, the second solenoid 880b is coupled to the sleeve 240 and thus automatically causes the sleeve 240 to insert (e.g. with the trocar 190) but not retract with the trocar 190 and/or to further insert the sleeve 240 within the distal airway of the neck (e.g. FIGS. 2A-2D).

FIG. 9A through FIG. 9D are images that illustrate different views of an example apparatus of FIG. 1A, according to an embodiment. In an embodiment, the apparatus 900 includes a palpation subsystem, a neck scanning device, and/or a pneumatic trocar subsystem. In an embodiment, the neck scanning device uses a horizontal linear stage motor 926 (motor 126) to translate a vertically actuated probe 902 (marker 190 or trocar 190) mounted to a carriage 920 by a holder 924. In one embodiment, motion in each axis is actuated by an actuator (e.g. motor 126 along the carriage guide 114 and neck and motor 192 in a direction orthogonal to the carriage guide 114 and neck). In an example embodiment, the motors 126, 192 are direct current (DC) motors, and each motor includes a linear sensor to measure a position along each respective axis. In an example embodiment, the linear sensor is a rotary encoder positioned on each motor and transmits the data indicating the position along each respective axis to a controller positioned within a housing 906 (processor 140). In some embodiments, the apparatus 900 includes the collar 542 that is secured to the neck at 904 in FIG. 9A (e.g. block 905 that simulates a neck). In an embodiment, various portions of the apparatus 900, such as the collar 542 or frame 110, marker 190 or probe, and sensor 122, were fabricated in poly-lactic acid (FLA) using fused deposition modeling (FDM).

The apparatus 900 includes the controller (module 150) within the housing 906 (processor 140) configured to monitor motor characteristics, such as current drawn. In one embodiment, the controller is an Adafruit Metro M0 Express (Adafruit, N.Y.) with a Toshiba Dual TB9051FTG Motor Driver (Toshiba, Japan). In an embodiment, the apparatus 900 is powered by a 12 volt (V) rechargeable battery supply, although other power sources are feasible. The apparatus 900 is further configured to stimulate trocar insertion using an insertion actuator (marker 190), such as a piston of a single-acting, spring return pneumatic cylinder 902 (Bimba, Ill.) of the current embodiment. In an embodiment, the pneumatic cylinder 902 is secured to the carriage 920 by the holder 924, where the carriage 920 moves along the carriage guide 914. In an embodiment, the pneumatic cylinder 902 is fluidly coupled to a pressurized fluid source within the housing 906 via a regulator and valve to control the flow of fluid and pressure. In the current device, the regulator is a 60 pound per square inch (psi) regulator (Poseidon Brands, Ark.), the pressurized fluid sources is a Carbon Dioxide (CO2) cartridge (APGR Green Inc., Arkansas) and the valve is a 12V solenoid valve (Grainger, Ill.).

The apparatus 900 includes a system and method of locating the cricothyroid membrane. One embodiment of the system includes training a model, including machine learning techniques, to predict the location of the cricothyroid membrane. In an example embodiment, a validation sensor is used to determine the actual location of the cricothyroid membrane. The apparatus 900 is then attached to multiple subjects to predict the location of the cricothyroid membrane of each subject (e.g. using criteria with the input data from the sensor 122) and this is compared with the actual location of the cricothyroid membrane e.g. determined with validation sensors). Based on this comparison, the model is improved so that the criteria for predicting the location of the cricothyroid membrane based on the input data (e.g. sensor data of topographical data of the neck along the carriage guide 114) are selected to more accurately predict the location of the cricothyroid membrane. The accuracy of the model used in the embodiments of the present invention is 98%. In an embodiment, the apparatus 900 (module 150) measures the parameter value of each subject and this parameter value data is compared with the data from the validation sensor (provides the actual location of the cricothyroid membrane) so that the measured parameter value at each incremental position is assigned a positive (cricothyroid membrane present) or negative (cricothyroid membrane not present) value. In an embodiment, the parameter value data from the multiple subjects is stored in a database and this database is used to generate a prediction model that is used to generate a prediction of a location of the cricothyroid membrane along the carriage guide based on input data of parameter values of topographical data, of the neck of a subject along the carriage guide.

Following user initiation of the scan, the motorized probe E, sensor 122) inside the sensing car (carriage 120) extends downward, pushing on the neck until the probe reaches a pre-set pressure measured by the motor impedance (e.g. motor 126 impedance monitored by the processor 140) in real time. In an embodiment, the probe then retracts a certain distance (e.g. about 5.0 millimeters or mm) and the horizontal linear actuator (motor 126) moves the sensing car forward an incremental distance (e.g. 2.0 mm). The scan continues until the sensing car reaches the end of the track. A machine learning algorithm (MLA), using one or more instructions of the control module 150, then calculates the predicted cricothyroid membrane region and the position corresponding to the center of that region is sent to the controller within the housing 906. In an embodiment, when the encoder readings match the position received by the controller, the pneumatic cylinder 902 is deployed to either mark or insert (e.g. depending on whether the marker 190 or trocar 190 is actuated by the pneumatic cylinder 902) through the skin of the neck.

Figure 9A:
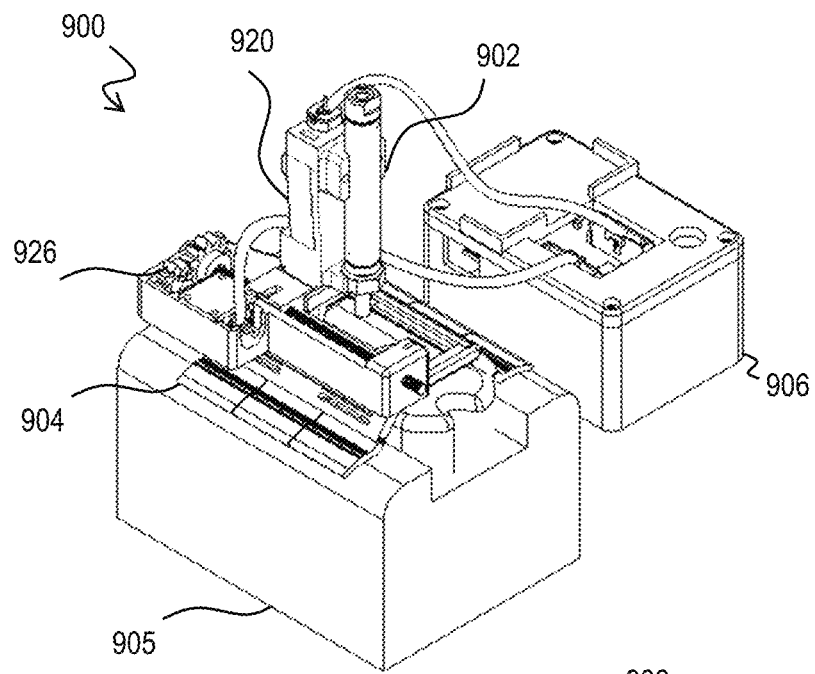
FIG. 9A through FIG. 9D are images that illustrate different views of an example apparatus of FIG. 1A, according to an embodiment.
Figure 9B:
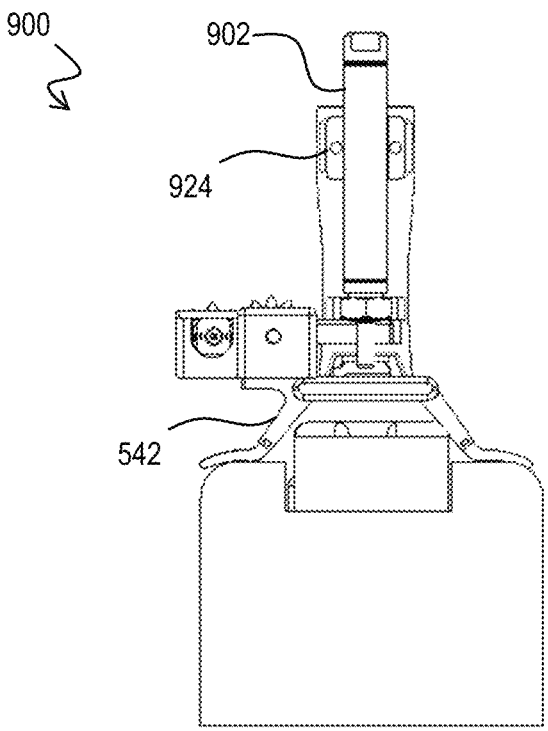
Figure 9C:
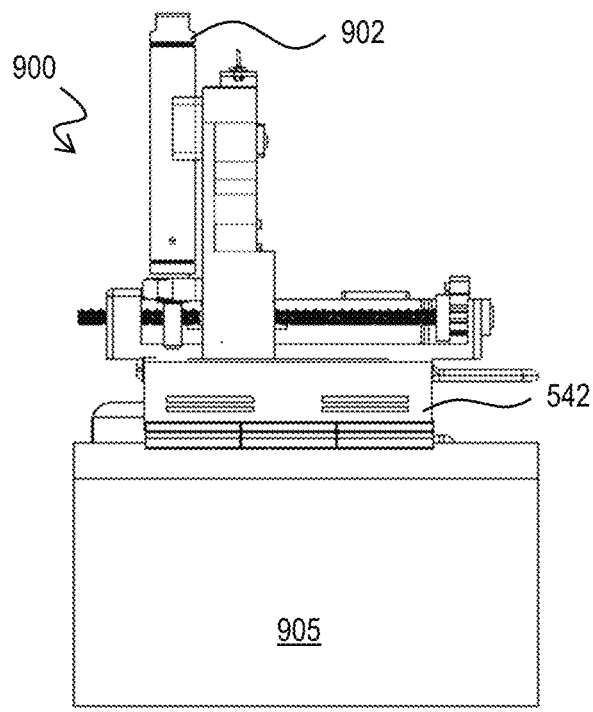
Figure 9D:
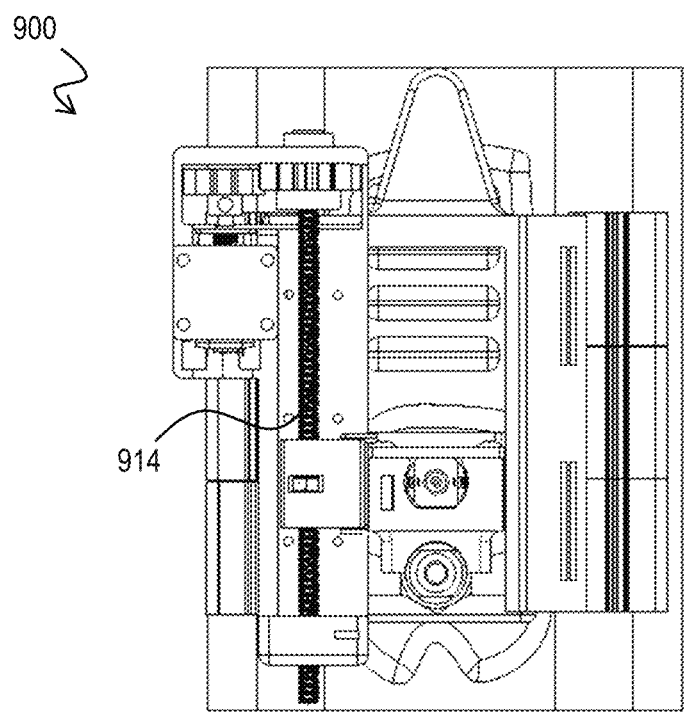
Figure 9E:
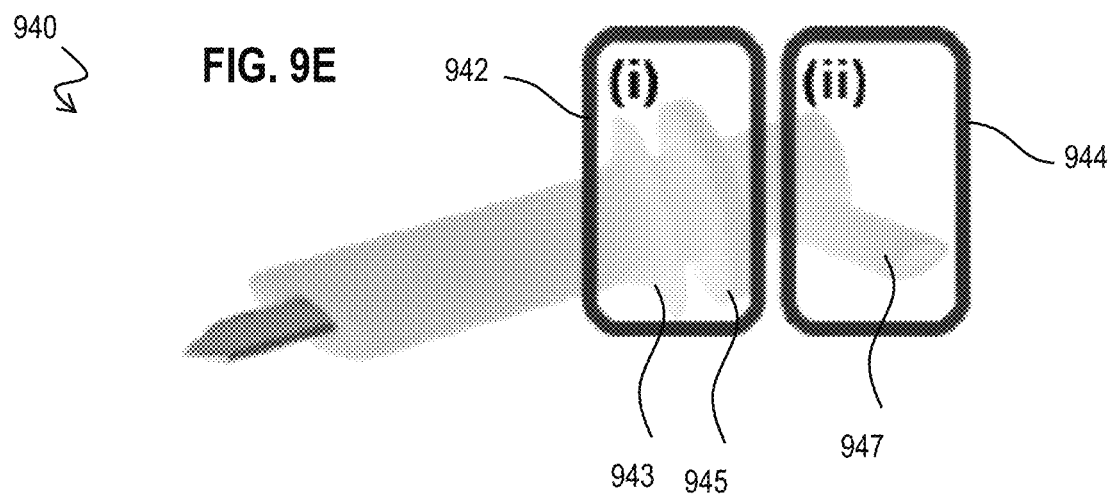
FIG. 9E through FIG. 9F are images that illustrate different views of an example trocar used in the apparatus of FIGS. 9A-9D, according to an embodiment.
Figure 9F:
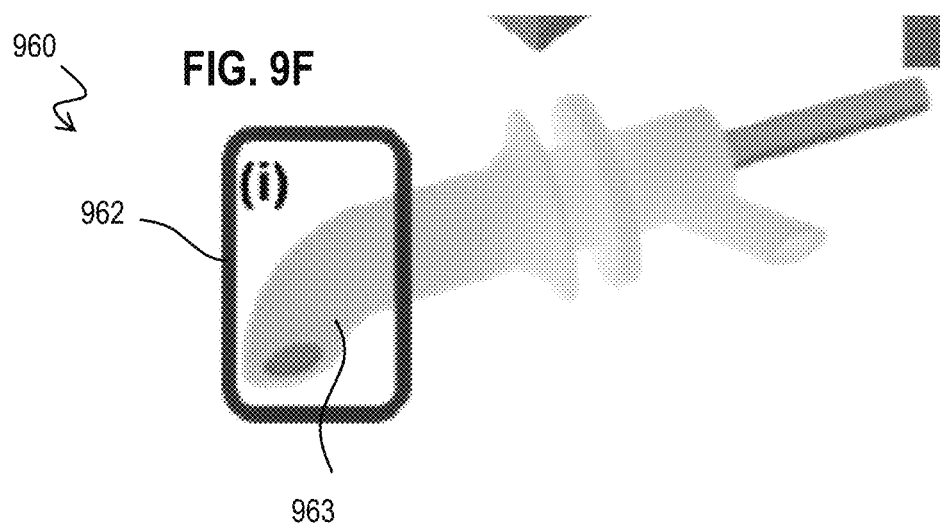

In an embodiment, the sensor 122 of the apparatus 900 is a mechanical palpation system and the carriage holds a pneumatic marking system as a surrogate for a trocar. FIG. 9E and FIG. 9F depict the sleeve 940, 960 which guides the oxygen catheter into the incised airway and will be included in more advanced iterations of the EO2 device. In an embodiment, the sleeve 940 features a region 942 with a disk-like tab 945 to prevent the sleeve 940 from falling into the created airway and includes a more conical shaped stopper 943 ahead to prevent the sleeve from coming out of the neck when the trocar 190 is retracted. In another embodiment, the sleeve 940 features a region 944 that includes a side port 947 for the oxygen catheter to enter the emergency airway created through the neck of the subject after the trocar 190 is retracted. FIG. 9F illustrates an embodiment of a trocar 190 being retracted from the sleeve 960 following incision. In an embodiment, the sleeve 960 includes a flexible bend 963 in a distal region 962 to allow the sleeve 960 to straighten when mounted on the trocar 190 during incision and to bend when in the throat to guide in the oxygen catheter.

Figure 10A:
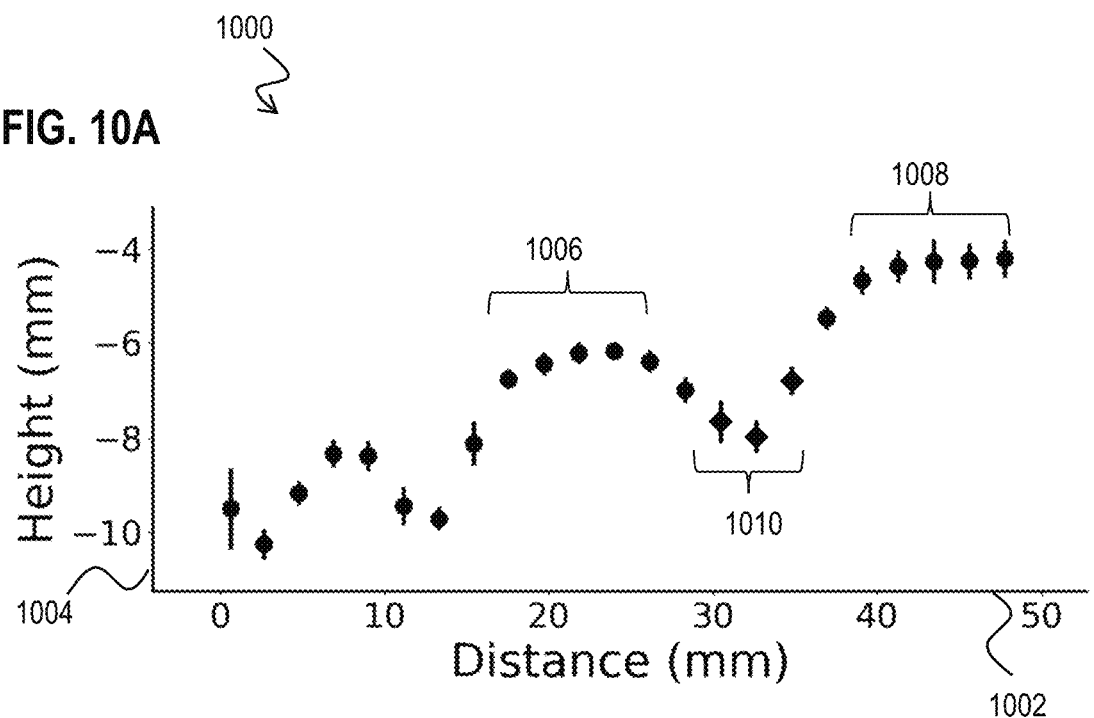
FIG. 10A is a graph that illustrates an example of topographical data of a neck of the subject measured by the sensor of FIG. 1A at incremental positions over a range of the neck, according to an embodiment.

FIG. 10A is a graph 1000 that illustrates an example of topographical data of a neck of the subject measured by the sensor of FIG. 1A at incremental positions over a range of the neck, according to an embodiment. The horizontal axis 1002 is distance in units of millimeters (mm). The vertical axis 1004 is distance in units of millimeters (mm). For purposes of FIG. 10A, "height" along the vertical axis 1004 and measured by the sensor 122 is defined as a magnitude of the distance between the sensor 122 and the surface of the neck 195 and the sign is negative. In an embodiment, the graph 1000 plots values of the parameters received by the processor 140 from the sensor 122 as the carriage 120 moves over the carriage guide 114. In an embodiment, the carriage guide 114 has a range which extends from one end that is adjacent the sternal notch to a second end adjacent the thyroid cartilage so that the measured height by the sensor 122 varies from a high negative value (e.g. adjacent the sternal notch where the surface of the neck is relatively far from the sensor 122) to a low negative value (e.g. adjacent the thyroid cartilage where the surface of the neck is relatively close to the sensor 122). In an embodiment, the processor 140 and module 150 includes instructions to determine the location of the cricothyroid membrane 1010 based on the data of the graph 1000. In one embodiment, the processor 140 and module 150 determines the cricoid cartilage region 1006 based on a region with relatively constant first height value, the thyroid cartilage region 1008 based on a region with relatively constant second height value greater than the first height value in the cricoid cartilage region 1006 and the cricothyroid membrane region 1010 between the regions 1006, 1008 and with height value that is less than both regions 1006, 1008. In another embodiment, the processor 140 and module 150 determines the cricothyroid membrane region 1010 by measuring values of on one or more of the parameters discussed below with respect to FIG. 10B at each incremental position.

Figure 10B:
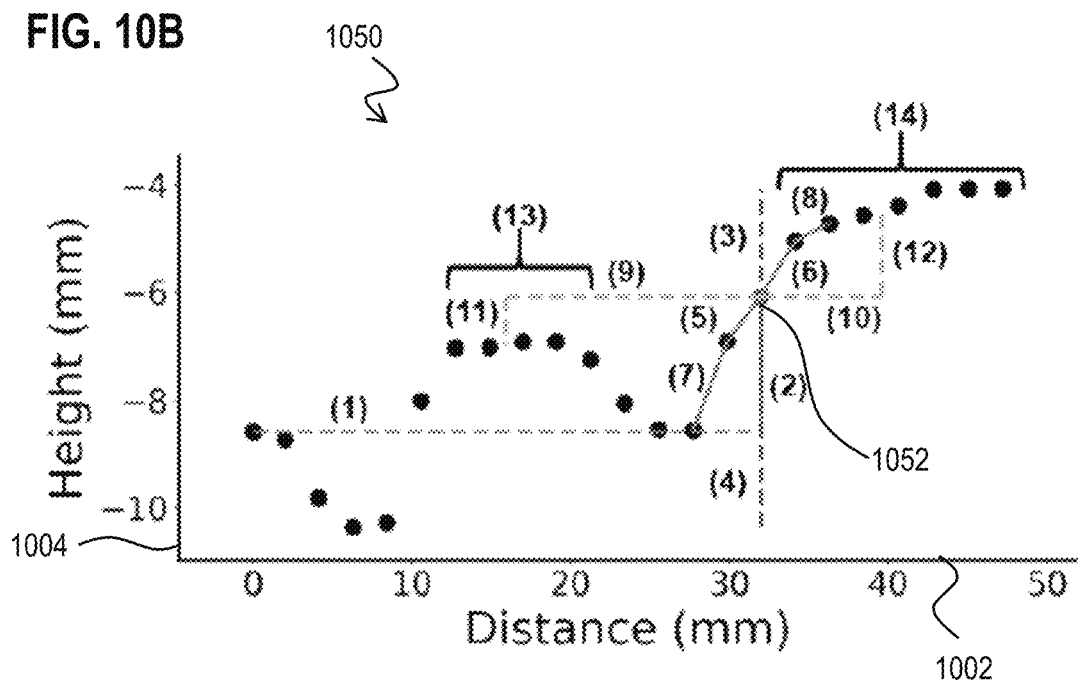
FIG. 10B is a graph that illustrates an example of multiple parameters determined for each incremental position of FIG. 10A along the range of the neck, according to an embodiment.

FIG. 10B is a graph that illustrates an example of multiple parameters determined for each incremental position of FIG. 10A along the range of the neck, according to an embodiment. The horizontal axis 1002 is distance in units of millimeters (mm). The vertical axis 1004 is distance in units of millimeters (mm). In an embodiment, for each incremental position along the carriage guide 114 that the sensor 122 measures the value of the parameter indicating the topography of the neck, the sensor 122 and/or the processor 140 determine one or more further values of the following parameters in the control module 150 and/or in steps 455-459. FIG. 10B depicts a current position 1052 and each of the parameters is depicted with respect to this current position 1052, however each of these parameters can be computed for each incremental position along the carriage guide 114. Each parameter is represented in FIG. 10B by a bracketed number. In one embodiment, a first parameter is (1) a distance from a start point along the carriage guide 114 to the current position 1052. In another embodiment, a second parameter (2) is a height from a starting point to the current position 1052. In another embodiment, a third parameter (3) is a height from the current position 1052 to a maximum height point. In another embodiment, a fourth parameter (4) is a height from the current position 1052 to a minimum preceding point. In another embodiment, a fifth parameter (5) is a slope before the current position 1052. In another embodiment, a sixth parameter (6) is a slope after the current position 1052. In another embodiment, a seventh parameter (7) is a slope before the preceding point. In another embodiment, an eighth parameter (8) is a slope after a following point. In another embodiment, a ninth parameter (9) is a distance between the current position 1052 and a preceding plateau. In another embodiment, a tenth parameter (10) is a distance between the current position 1052 and a following plateau. In another embodiment, an eleventh parameter (11) is a height between a preceding plateau and the current position 1052. In another embodiment, a twelfth parameter (12) is a height between a following plateau and the current position 1052. In another embodiment, a thirteenth parameter (13) is a size of the preceding plateau. In another embodiment, a fourteenth parameter (14) is a size of the following plateau.

In an embodiment, in step 459 the module 150 determines the second data or position along the carriage guide 114 corresponding to the cricothyroid membrane based on an input first data or value of the parameter indicating the topography of the neck as the carriage 120 moves on the carriage guide 114. In one embodiment, in step 459 the module 150 determines the position along the carriage guide 114 corresponding to the cricothyroid membrane by assigning a probability (e.g. 1 for yes, 0 for no) of a presence of the cricothyroid membrane at each incremental position along the carriage guide 114 of the input first data. The module 150 assigns the probability to each incremental position along the carriage guide 114 of the input first data, based on the machine learning (ML) model and Support Vector Machine (SVM) discussed below. In one example embodiment, in step 459 the module 150 determines the position along the carriage guide 114 corresponding to the cricothyroid membrane based on a continuous range of incremental positions along the carriage guide 114 of the input first data with a positive probability (e.g. 1) of the presence of the cricothyroid membrane. In an example embodiment, where the module 150 determines a continuous range of incremental positions with the positive probability, the module 150 determines one of an average or mean within the range as the position along the carriage guide 114 corresponding to the cricothyroid membrane. In another example embodiment, where the module 150 determines more than one continuous range of incremental positions with the positive probability, the module 150 chooses the continuous range of incremental positions as corresponding to the CTM based on an average value (e.g. higher value) of the topography parameter.

In an embodiment, the system trains a model, with machine learning (ML) techniques, to predict the location of the cricothyroid membrane. Prior to training the (ML) model, steps 451 through 457 are performed for a number (e.g. 100) of subjects to measure the value of the topography parameter (e.g. height) at each incremental position of the neck of each subject. In an example embodiment, these data values of the topography parameter of the necks of all subjects (e.g. 2300 data values at 2300 incremental positions, 23 incremental positions for each of the 100 subjects) are stored in a memory of the processor 140. In an example embodiment, the topography parameter values from each subject are split into varying lengths and each incremental position is subtracted by the x-starting point for the respective subject to replicate scans starting and ending in different positions on the model. This step introduces variation in the data and prevents over-fitting. In an embodiment, for each subject, external validation is performed so that each incremental position along the carriage guide 114 is positively (e.g. 1) or negatively (e.g. 0) labelled based on whether each incremental position falls within (positively) or outside (negatively) the CTM. In an example embodiment, the external validation is performed by visual confirmation and/or with external sensors (e.g. radiological sensors) to determine the presence or lack of presence of the CTM at each incremental position. In an example embodiment, after classification at each incremental position, one or more of the fourteen (1)-(14) parameter values discussed above with respect to FIG. 10B are computed for each incremental position and these one or more parameter values are also stored in the memory of the processor 140. Features extracted from the data are first normalized [6], [7]. An exhaustive search is then performed on the training data-set to identify the ideal cost and gamma parameters [6], [8]. A Support Vector Machine with a rbf kernel, cost parameter=464.158 and gamma=0.0356 is then trained and tested on respective subsets of data [6], [9]. The resulting trained model has an accuracy of 98.72% and is used by the module 150 in step 459 to classify incremental positions of input first data as part of the cricothyroid membrane (1) or not part of the membrane (0). The trained model was also implemented with the mechanical subsystems. The predictions are used by the module 150 to group the incremental positions of the carriage guide 114 into possible CTM regions, and if multiple regions exist, post-processing algorithms choose the region most likely to be the CTM based on the average height (e.g. has the highest average height below a provided maximum value) of the region and number of points (e.g. 6 or less points) in the group.

3. HARDWARE OVERVIEW

FIG. 11 is a block diagram that illustrates a computer system 1100 upon which an embodiment of the invention may be implemented. Computer system 1100 includes a communication mechanism such as a bus 1110 for passing information between other internal and external components of the computer system 1100. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1100, or a portion thereof, constitutes a means for performing one or more steps of one or more methods described herein.

A sequence of binary digits constitutes digital data that is used to represent a number or code for a character. A bus 1110 includes many parallel conductors of information so that information is transferred quickly among devices coupled to the bus 1110. One or more processors 1102 for processing information are coupled with the bus 1110. A processor 1102 performs a set of operations on information. The set of operations include bringing information in from the bus 1110 and placing information on the bus 1110. The set of operations also typically include comparing two or more units of information, shifting positions of units of information, and combining two or more units of information, such as by addition or multiplication. A sequence of operations to be executed by the processor 1102 constitutes computer instructions.

Computer system 1100 also includes a memory 1104 coupled to bus 1110. The memory 1104, such as a random access memory (RAM) or other dynamic storage device, stores information including computer instructions. Dynamic memory allows information stored therein to be changed by the computer system 1100. RAM allows a unit of information stored at a location called a memory address to be stored and retrieved independently of information at neighboring addresses. The memory 1104 is also used by the processor 1102 to store temporary values during execution of computer instructions. The computer system 1100 also includes a read only memory (ROM) 1106 or other static storage device coupled to the bus 1110 for storing static information, including instructions, that is not changed by the computer system 1100. Also coupled to bus 1110 is a non-volatile (persistent) storage device 1108, such as a magnetic disk or optical disk, for storing information, including instructions, that persists even when the computer system 1100 is turned off or otherwise loses power.

Information, including instructions, is provided to the bus 1110 for use by the processor from an external input device 1112, such as a keyboard containing alphanumeric keys operated by a human user, or a sensor. A sensor detects conditions in its vicinity and transforms those detections into signals compatible with the signals used to represent information in computer system 1100. Other external devices coupled to bus 1110, used primarily for interacting with humans, include a display device 1114, such as a cathode ray tube (CRT) or a liquid crystal display (LCD), for presenting images, and a pointing device 1116, such as a mouse or a trackball or cursor direction keys, for controlling a position of a small cursor image presented on the display 1114 and issuing commands associated with graphical elements presented on the display 1114.

In the illustrated embodiment, special purpose hardware, such as an application specific integrated circuit (IC) 1120, is coupled to bus 1110. The special purpose hardware is configured to perform operations not performed by processor 1102 quickly enough for special purposes. Examples of application specific ICs include graphics accelerator cards for generating images for display 1114, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1100 also includes one or more instances of a communications interface 1170 coupled to bus 1110. Communication interface 1170 provides a two-way communication coupling to a variety of external devices that operate with their own processors, such as printers, scanners and external disks. In general the coupling is with a network link 1178 that is connected to a local network 1180 to which a variety of external devices with their own processors are connected. For example, communication interface 1170 may be a parallel port or a serial port or a universal serial bus (USB) port on a personal computer. In some embodiments, communications interface 1170 is an integrated services digital network (ISDN) card or a digital subscriber line (DSL) card or a telephone modem that provides an information communication connection to a corresponding type of telephone line. In some embodiments, a communication interface 1170 is a cable modem that converts signals on bus 1110 into signals for a communication connection over a coaxial cable or into optical signals for a communication connection over a fiber optic cable. As another example, communications interface 1170 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1170 sends and receives electrical, acoustic or electromagnetic signals, including infrared and optical signals, that carry information streams, such as digital data.

The term computer-readable medium is used herein to refer to any medium that participates in providing information to processor 1102, including instructions for execution. Such a medium may take many forms, including, but not limited to, non-volatile media, volatile media and transmission media. Non-volatile media include, for example, optical or magnetic disks, such as storage device 1108. Volatile media include, for example, dynamic memory 1104. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1102, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1102, except for carrier waves and other signals.

Logic encoded in one or more tangible media includes one or both of processor instructions on a computer-readable storage media and special purpose hardware, such as ASIC \*1120.

Network link 1178 typically provides information communication through one or more networks to other devices that use or process the information. For example, network link 1178 may provide a connection through local network 1180 to a host computer 1182 or to equipment 1184 operated by an Internet Service Provider (ISP). ISP equipment 1184 in turn provides data communication services through the public, world-wide packet-switching communication network of networks now commonly referred to as the Internet 1190. A computer called a server 1192 connected to the Internet provides a service in response to information received over the Internet. For example, server 1192 provides information representing video data for presentation at display 1114.

The invention is related to the use of computer system 1100 for implementing the techniques described herein. According to one embodiment of the invention, those techniques are performed by computer system 1100 in response to processor 1102 executing one or more sequences of one or more instructions contained in memory 1104. Such instructions, also called software and program code, may be read into memory 1104 from another computer-readable medium such as storage device 1108. Execution of the sequences of instructions contained in memory 1104 causes processor 1102 to perform the method steps described herein. In alternative embodiments, hardware, such as application specific integrated circuit 1120, may be used in place of or in combination with software to implement the invention. Thus, embodiments of the invention are not limited to any specific combination of hardware and software.

The signals transmitted over network link 1178 and other networks through communications interface 1170, carry information to and from computer system 1100. Computer system 1100 can send and receive information, including program code, through the networks 1180, 1190 among others, through network link 1178 and communications interface 1170. In an example using the Internet 1190, a server 1192 transmits program code for a particular application, requested by a message sent from computer 1100, through Internet 1190, ISP equipment 1184, local network 1180 and communications interface 1170. The received code may be executed by processor 1102 as it is received, or may be stored in storage device 1108 or other non-volatile storage for later execution, or both. In this manner, computer system 1100 may obtain application program code in the form of a signal on a carrier wave.

Various forms of computer readable media may be involved in carrying one or more sequence of instructions or data or both to processor 1102 for execution. For example, instructions and data may initially be carried on a magnetic disk of a remote computer such as host 1182. The remote computer loads the instructions and data into its dynamic memory and sends the instructions and data over a telephone line using a modem. A modem local to the computer system 1100 receives the instructions and data on a telephone line and uses an infra-red transmitter to convert the instructions and data to a signal on an infra-red a carrier wave serving as the network link 1178. An infrared detector serving as communications interface 1170 receives the instructions and data carried in the infrared signal and places information representing the instructions and data onto bus 1110. Bus 1110 carries the information to memory 1104 from which processor 1102 retrieves and executes the instructions using some of the data sent with the instructions. The instructions and data received in memory 1104 may optionally be stored on storage device 1108, either before or after execution by the processor 1102.

FIG. 12 illustrates a chip set 1200 upon which an embodiment of the invention may be implemented. Chip set 1200 is programmed to perform one or more steps of a method described herein and includes, for instance, the processor and memory components described with respect to FIG. *11 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1200, or a portion thereof, constitutes a means for performing one or more steps of a method described herein.

In one embodiment, the chip set 1200 includes a communication mechanism such as a bus 1201 for passing information among the components of the chip set 1200. A processor 1203 has connectivity to the bus 1201 to execute instructions and process information stored in, for example, a memory 1205. The processor 1203 may include one or more processing cores with each core configured to perform independently. A multi-core processor enables multiprocessing within a single physical package. Examples of a multi-core processor include two, four, eight, or greater numbers of processing cores. Alternatively or in addition, the processor 1203 may include one or more microprocessors configured in tandem via the bus 1201 to enable independent execution of instructions, pipelining, and multithreading. The processor 1203 may also be accompanied with one or more specialized components to perform certain processing functions and tasks such as one or more digital signal processors (DSP) 1207, or one or more application-specific integrated circuits (ASIC) 1209. A DSP 1207 typically is configured to process real-world signals (e.g., sound) in real time independently of the processor 1203. Similarly, an ASIC 1209 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1203 and accompanying components have connectivity to the memory 1205 via the bus 1201. The memory 1205 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1205 also stores the data associated with or generated by the execution of one or more steps of the methods described herein.

4. ALTERNATIVES, DEVIATIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

5. REFERENCES

[1] World Wide Web file 1107258 in folder fullarticle in subdomain jamasurgery in subdomain journals in domain jamanetwork in top level domain corn.

[2] Pugh H E, LeClerc S, and Mclennan J, "A review of pre-admission advanced airway management in combat casualties, Helmand Province 2013," J. R. Army Med. Corps, vol. 161, no. 2, pp. 121-6, 2015.

[3] L. H. PITTS, J. KAKTIS, J. CARONNA, S. JENNETT, and J. T. HOFF, "Brain Death, Apneic Diffusion Oxygenation, and Organ Transplantation," J. Trauma Acute Care Surg., vol. 18, no. 3, 1978.

[4] World Wide web file 28915219 in folder pubmed in subdomain ncbi of subdomain nlm of domain nih in top level domain gov

[5] World Wide web file PMC3704966 in folder articles in subdomain pmc in subdomain ncbi in subdomain nlm in domain nih in top level domain gov.

[6] Scikit-learn: Machine Learning in Python. Pedregosa et al., MLR 12, pp. 2825-2830, 2011

[7] World Wide web file sklearn of subdomain preprocessing of subdomain StandardScaler of top level domain html in folder generated in folder modules in subdomain scikit-learn of top level domain org.

[8] World Wide web file sklearn of subdomain model selection of subdomain GridSearchCV of top level domain html in folder generated in folder modules in subdomain scikit-learn of top level domain org.

[9] World Wide web file svm of top level domain html in folder modules in folder stable in subdomain scikit-learn of top level domain org.

What is claimed is:

1. An apparatus comprising:
   a frame including a carriage guide, wherein the frame is configured to be secured around a neck of a subject;
   a carriage including a sensor, wherein the carriage is configured to move along the carriage guide and wherein the sensor is configured to measure a value of a parameter indicating a topography of the neck of the subject;
   at least one processor communicatively coupled with the sensor; and
   at least one memory including one or more sequences of instructions,
   the at least one memory and the one or more sequences of instructions configured to, with the at least one processor, cause the apparatus to perform at least the following,
   receive first data from the sensor of the value of the parameter indicating the topography of the neck of the subject as the carriage is moved along the carriage guide,
   determine, with the first data, second data indicating a position along the carriage guide corresponding to the cricothyroid region of the neck, and
   transmit a first signal indicating the second data.

2. The apparatus of claim 1, further comprising a motor connected to the carriage and configured to cause the carriage to move along the carriage guide, wherein the at least one memory and the one or more sequences of instructions are further configured to cause the at least one processor to transmit a second signal to the motor to cause the carriage to automatically move along the carriage guide.

3. The apparatus of claim 2, wherein the motor is configured to cause the carriage to automatically move incremental distances along the carriage guide and wherein the sensor is configured to measure the value of the parameter at the incremental distances along the carriage guide.

4. The apparatus of claim 1, wherein the sensor is a motor impedance based sensing probe.

5. The apparatus of claim 1, wherein the sensor is a sensor assembly including a roller configured to engage the neck of the subject, an electronic force sensor and a shaft assembly configured to transmit forces from the roller to the electronic force sensor.

6. The apparatus of claim 1, wherein the sensor comprises a set of pins wherein one or more pins in the set of pins are configured to deflect in response to the topography of the neck of the subject.

7. The apparatus of claim 1, further comprising a holder affixed to the carriage and configured to removably hold at least one of a marker or a trocar.

8. A system comprising the apparatus of claim 7, further comprising the trocar disposed in the holder, wherein the trocar includes a handle configured to allow a user to manually insert the trocar through the cricothyroid region of the neck.

9. The system of claim 8, further comprising a position indicator to indicate a location of the trocar along the carriage guide, wherein the location of the trocar along the carriage guide is adjusted based on the second data.

10. The apparatus of claim 7, further comprising a motor connected to the trocar and configured to cause the trocar to insert through the cricothyroid membrane and wherein the at least one memory and the one or more sequences of instructions are further configured to cause the at least one processor to transmit a third signal to the motor to cause the trocar to automatically be inserted through the cricothyroid membrane.

11. The apparatus of claim 10, wherein the motor comprises a pneumatic cylinder fluidly coupled to a pressurized fluid source through at least one of a valve and pressure regulator.

12. A system comprising the apparatus of claim 7, further comprising:
   the trocar disposed in the holder;
   a first motor connected to the carriage and configured to cause the carriage to move along the carriage guide;
   a first linear sensor configured to measure movement of the carriage along the carriage guide in a first direction;
   a second motor connected to the trocar and configured to cause the trocar to be inserted through the cricothyroid membrane of the neck; and
   a second linear sensor configured to measure movement of the trocar along a second direction orthogonal to the first direction;
   wherein the at least one processor is communicatively coupled to the first motor, the first linear sensor, the second motor and the second linear sensor;
   and wherein the at least one memory and the one or more sequences of instructions are further configured to cause the at least one processor to transmit a second signal to the first motor to cause the carriage to automatically move along the carriage guide and to transmit a third signal to the second motor to cause the trocar to automatically be inserted through the cricothyroid membrane upon the at least one processor receiving data from the first linear sensor indicating that the trocar is positioned at the position along the carriage guide corresponding to the cricothyroid membrane.

13. A system comprising the apparatus of claim 7, further comprising the marker disposed in the holder, wherein the marker is configured to allow a user to manually mark the cricothyroid region of the neck.

14. The system of claim 13, further comprising a position indicator to indicate a location of the marker along the carriage guide, wherein the location of the marker along the carriage guide is adjusted based on the second data.

15. The apparatus of claim 7, further comprising a motor connected to the marker and configured to cause the marker to mark the cricothyroid membrane and wherein the at least one memory and the one or more sequences of instructions are further configured to cause the at least one processor to transmit a third signal to the motor to cause the marker to automatically mark the cricothyroid membrane.

16. The apparatus of claim 15, wherein the motor comprises a pneumatic cylinder fluidly coupled to a pressurized fluid source through at least one of a valve and pressure regulator.

17. A system comprising the apparatus of claim 7, further comprising:
   the marker disposed in the holder;
   a first motor connected to the carriage and configured to cause the carriage to move along the carriage guide;
   a first linear sensor configured to measure movement of the carriage along the carriage guide in a first direction;
   a second motor connected to the marker and configured to cause the marker to mark the cricothyroid membrane of the neck; and
   a second linear sensor configured to measure movement of the marker along a second direction orthogonal to the first direction;

wherein the at least one processor is communicatively coupled to the first motor, the first linear sensor, the second motor and the second linear sensor;

and wherein the at least one memory and the one or more sequences of instructions are further configured to cause the at least one processor to transmit a second signal to the first motor to cause the carriage to automatically move along the carriage guide and to transmit a third signal to the second motor to cause the marker to automatically mark the cricothyroid membrane upon the at least one processor receiving data from the first linear sensor indicating that the marker is positioned at the position along the carriage guide corresponding to the cricothyroid membrane.

18. An apparatus of claim 1, further comprising an attachment configured to secure the frame around the neck of the subject.

19. An apparatus of claim 18, wherein the attachment is a strap and wherein the frame defines one or more strap openings configured to secure the strap, wherein the one or more strap openings are oriented parallel to the carriage guide.

20. An apparatus of claim 1, wherein the frame is a collar comprising:
a central frame with side rails and defining a central opening; and
a pair of wings outside the side rails, wherein the wings are shaped to accommodate an arcuate surface of the neck of the subject;
wherein the side rails and central opening are the carriage guide.

21. An apparatus of claim 20, wherein the side rails and the central opening are oriented parallel to each other and parallel to the neck of the subject when the frame is secured around the neck of the subject and wherein the wings are made from flexible material.

22. A method comprising:
securing, with an attachment, a frame around a neck of a subject, wherein the frame includes a carriage guide;
moving a carriage along the carriage guide;
measuring, with a sensor of the carriage, a value of a parameter indicating a topography of the neck of the subject as the carriage moves along the carriage guide;
automatically receiving, at a processor, first data from the sensor indicating the topography of the neck of the subject as the carriage moves along the carriage guide;
automatically determining, with the processor, second data based on the first data, said second data indicating a position along the carriage guide corresponding to the cricothyroid region of the neck, and
transmitting, with the processor, a first signal indicating the second data.

23. A method of claim 22, further comprising:
inserting a trocar and sleeve through the cricothyroid membrane of the neck based on the first signal;
retracting the trocar from the subject; and
introducing an oxygen catheter through the sleeve and into an airway of the neck.

24. A method of claim 23, wherein a position indicator is provided that indicates a location of the trocar along the carriage guide, wherein the method further comprises:
manually aligning, with the position indicator, the location of the trocar along the carriage guide to be aligned with the position along the carriage guide corresponding to the cricothyroid region of the neck; and
manually inserting, with a handle, the trocar and sleeve through the cricothyroid membrane of the neck based on the manually aligning step.

25. A method of claim 23, further comprising:
automatically aligning, with a first motor connected to the carriage, the trocar with the position along the carriage guide corresponding to the cricothyroid region of the neck; and
automatically inserting, with a second motor connected to the trocar, the trocar and sleeve through the cricothyroid membrane of the neck.

* * * * *